(12) United States Patent
Chavez et al.

(10) Patent No.: US 9,458,506 B2
(45) Date of Patent: Oct. 4, 2016

(54) MARKERS FOR THE DETECTION OF HUMAN EMBRYO DEVELOPMENTAL QUALITY

(71) Applicant: The Board of Trustees of the Leland Stanford Junior University, Palo Alto, CA (US)

(72) Inventors: Shawn L. Chavez, Fremont, CA (US); Renee A. Reijo Pera, Bozeman, MT (US); Sohyun L. McElroy, Stanford, CA (US); Barry Behr, Palo Alto, CA (US); Lynn M. Westphal, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/528,927

(22) Filed: Oct. 30, 2014

(65) Prior Publication Data
US 2015/0119282 A1    Apr. 30, 2015

Related U.S. Application Data

(60) Provisional application No. 61/898,325, filed on Oct. 31, 2013.

(51) Int. Cl.
*C12Q 1/68*    (2006.01)
(52) U.S. Cl.
CPC ....... *C12Q 1/6883* (2013.01); *C12Q 2600/158* (2013.01)
(58) Field of Classification Search
None
See application file for complete search history.

(56) References Cited

PUBLICATIONS

Adona P.R. et al., "Embryonic Development and Gene Expression in Oocytes Culture in Vitro in Supplemented Pre-Maturation and Maturation Media" Reprod Dom Anim. 46, e31-e38 (2011).
Golding M. C., et al., "Analysis of DNA (cyosine 5) methyltransferase mRNA sequence and expression in bovine preimplantation embryos, fetal and adult tissues" Gene Expression Patterns 3 (2003) 551-558.
Huntriss J. et al., "Expression of mRNAs for DNA Methyltransferases and Methl-CpG-Binding Proteins in the Human Female Germ Line, Preimplantation Embryos, and Embryonic Stem Cells" Molecular Reproduction 2004, 323-336.
Jones P. L. et al., Methylated DNA and MeCP2 recruit histone deacetylase to repress transcription Nature Genetics (1998).
Katari S. et al., "DNA methylation and gene expression differences in children conceived in vitro or in vivo" Human Molecular Genetics, (2009) vol. 18, No. 20. p. 3769-3778.
Kawamura K. et al., "Ovarian brain-derived neurotrophic factor (BDNF) promotes the development of oocytes into preimplantation embyros" (Jun. 2005) vol. 102, No. 26, p. 9206-9211.
Kawamura K. et al., "Completion of Meiosis I of preovulatory oocytes and facilitation of preimplantation embryo development by glial cell line-derived neurotrophic factor." Developmental Biology 315 (2008) 189-202.
Latham et al., "Cross-regulation of histone modificiations" Nature Structural & Molecular Biology (2007).
Lewis et al., "Purification, Sequence, and Cellular Localization of a Novel Chromosomal Protein that Binds to Methylated DNA" Cell, vol. 69, 905-914, (Jun. 1992).
Linher-Melville et al., "The roles of glial cell line-derived neurotrophic factor, brain-derived neurotrophic factor and nerve growth factor during the final stage of folliculogenesis: a focus on oocyte maturation." Reproduction (2013).
Liu et al., "Regulation of histone H3 lysine 9 methylation in oocytes and early pre-implantation embryos" Development 131, 2269-2280 (2004).
May et al., "Multiplex RT-PCR Expression Analysis of Developmentally Important Genes in Individual Mouse Preimplantation Embryos and Blastomeres" Biology of Reproduction. 80, 194-202 (2009).
McElroy et al., "Parthenogenic Blastocysts Derive from Cumulus-Free in Vitro Matured Human Oocytes" (Jun. 2010).
Nan et al., "Transcriptional repression by the methyl-CpG-binding protein MeCP2 invovles a histone deacetylase complex" (Apr. 1998) Nature.
Qiao et al., "Changes in histone methylation during human oocyte maturation and IVF- or ICSI-derived embryo development" Fertile Sterile 93, 1628-1636 (2010).
Robert et al., "DNMT1 is required to maintain CpQ methylation and aberrant gene silencing in human cancer cells" Nature Genetics (2003) p. 61-65.
Sarmento et al., "Dynamic alterations of specific histone modificaitons during early murine development" Journal of Cell Science 117, 4449-4459 (2004).
Seisenberger et al., "Reprogramming DNA methylation in the mamalian life cycle: building and breaking epigenetic barriers" Philosophical Transactions of the Royal Society (2013).
Torres-Padilla et al., "Histone arginine methylation regulates cell fate and pluripotency in the early mouse embryo" Nature. (2007) 445(7124): 214-218.
Vassena et al., "Species-Dependent Expression Patterns of DNA Methyltransferase Genes in Mammalian Oocytes and Preimplantation Embryos" Molecular Reproduction and Development. 72:430-436 (2005).
Yu et al., "Effects of combined epidermal growth factor, brain-derived neurotrophic factor and insulin-like growth factor-I on human oocyte maturation and early fertilized and cloned embryo development." Human Reproduction, vol. 27, No. 7 pp. 2146-2159. (2012).
Zhao et al., "Gonadotrophin-induced paracrine regulation of human oocyte maturation by BDNF and GDNF secreted by granulosa cells" Human Reproduction, vol. 26, No. 3. pp. 695-702, (2011).
Zhang L. et al., "The role of brain-derived neurotrophic factor in mouse oocyte maturation in vitro involves activation of protein kinase B" Theriogenology (Jul. 2009) 73; 1096-1103.

*Primary Examiner* — Jim Ketter
(74) *Attorney, Agent, or Firm* — Pamela J. Sherwood; Bozicevic, Field & Francis LLP

(57) ABSTRACT

Markers are provided for genetic and epigenetic diagnosis of embryos to determine those of which are more likely to be chromosomally normal and advance in development.

6 Claims, 15 Drawing Sheets
(14 of 15 Drawing Sheet(s) Filed in Color)

MARKERS FOR THE DETECTION OF HUMAN EMBRYO DEVELOPMENTAL QUALITY

BACKGROUND OF THE INVENTION

The erasure and re-establishment of epigenetic marks (epigenetic reprogramming) is initiated in mammals during early pre-implantation development. Following fertilization, the paternal and maternal genomes are extensively modified and reset around the time of implantation, which is thought to be required to establish the totipotency of the newly formed embryo. The two main types of epigenetic modifications are DNA methylation and histone modifications, which work together to affect gene expression in a heritable manner (without altering DNA sequence) and influence chromatin structure (Lewis, J. D. et al. Cell 69, 905-914 (1992); Nan, X. et al. Nature 393, 386-389 (1998); Jones, P. L. et al. Nat Genet 19, 187-191 (1998)).

DNA methylation is mediated by a family of DNA methyltransferases (DNMTs) that catalyze the transfer of a methyl group to the 5'-position of cytosine residues within CpG dinucleotides usually resulting in effective gene silencing (Robert, M. F. et al. Nat Genet 33, 61-65 (2003)). Although global DNA methylation patterns in pre-implantation development have been documented in several species, the study of DNMT expression, particularly in early human embryos, is incomplete, with focus on just a few stages of pre-implantation development and/or particular DNMT family members (May, A. et al. Biol Reprod 80, 194-202 (2009); Golding, M. C. et al. Gene Expr Patterns 3, 551-558 (2003); Vassena, R. et al. Mol Reprod Dev 72, 430-436 (2005); Huntriss et al. Mol Reprod Dev 67, 323-336 (2004)).

Histone modifications include, but are not limited to, the phosphorylation of serine residues, acetylation of lysine residues and the methylation of either lysine or arginine residues, all of which are mediated by different histone-modifying enzymes and may affect biological outcome ((Latham et al. Nat Struct Mol Biol 14, 1017-1024 (2007)). While some studies have analyzed a subset of histone modifications in pre-implantation embryos from different species, data remains limited, especially in the human (Liu, H. et al. Development 131, 2269-2280 (2004); Torres-Padilla et al. Nature 445, 214-218 (2007); Qiao, J. et al. Fertil Steril 93, 1628-1636 (2010); Sarmento, O. F. et al. J Cell Sci 117, 4449-4459 (2004)).

Infertility is a common health problem that affects 10-15% of couples of reproductive-age. In the United States alone in the year 2006, approximately 140,000 cycles of in vitro fertilization (IVF) were performed. This resulted in the culture of more than a million embryos annually with variable, and often ill-defined, potential for implantation and development to term. The live birth rate, per cycle, following IVF was just 29%, while on average 30% of live births resulted in multiple gestations. Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

Previous studies have demonstrated that more than half of human embryos are aneuploid, carrying an abnormal chromosome number, which contributes to the low efficiency of in vitro fertilization (IVF). Traditional methods of evaluating IVF embryos involve subjective assessment of static morphologic criteria. Although there is a relationship between static embryo morphology and ploidy, the correlation has been weak. Consequently, multiple embryos with variable implantation potential may be transferred, leading to both high rates of embryonic loss and increased frequency of multiple gestations with higher maternal and perinatal risks.

In an effort to improve IVF success, clinics are increasingly using preimplantation genetic screening (PGS) in combination with growth to blastocyst stage to assist in selection of euploid embryos for transfer. However, extended culture of embryos may induce epigenetic changes during early embryogenesis, the long-term effects of which may be detrimental to offspring (Katari et al., Hum Mol Genet 2009 and others). In addition, the majority of data derived on human embryo development, by necessity is limited to that obtained from infertility clinics and embryos produced with germ cells that may be compromised. While such studies have proven to be invaluable, the interpretation of results and what should be considered "baseline" must be approached cautiously. Moreover, most studies of embryo development are conducted in the mouse or non-mammalian species, requiring extrapolation of results to human development. However, given extensive species-specific differences, even comparison between closely related mammalian species may be difficult. Thus, markers that can be identified and utilized or restored earliest in development with evidence of similar indications in fertile couples are of great clinical interest.

BRIEF SUMMARY OF THE INVENTION

Methods are provided for predicting blastocyst quality of a human embryo in vitro. Quality, as used herein, refers to the probability that an embryo will have a good morphology and is likely to remain euploid. Assessment of quality allows selection of healthy embryos for implantation. Such methods improve IVF procedures by allowing for early transfer of fewer, high quality embryos. These parameters can be used to select the optimal embryos for transfer, cryo-preservation, or for additional pre-implantation genetic diagnosis (PGD) analysis during an IVF procedure.

Prior to implantation of an embryo, e.g. beginning at the 4- to 8-cell stage, altered expression of proteins associated with epigenetic regulators of gene expression, including DNA methylation and histone modification, or mRNAs encoding such proteins, are indicative of the developmental quality potential of the embryo. Developmental quality includes the development of undesirable aneuploidy at the blastocyst stage. Analysis of epigenetic regulators of gene expression provides a means for prediction of blastocyst quality, and is useful in embryo selection for implantation; allowing selection of embryos for transfer with a greater potential for euploidy.

In some embodiments of the invention, a cell of a human embryo, usually a cell from at least the 4 cell stage and prior to the blastocyst stage, is analyzed for the presence of a protein or mRNA associated with epigenetic regulation of gene expression, where altered levels of the protein or corresponding mRNA are indicative of the embryo quality. In some embodiments, following analysis, an embryo is selected, or not selected, for transfer based on the assessment of quality. In some embodiments, the protein associated with epigenetic regulation of gene expression is one or more of ATF2, KAT5, MSK2, PRMT5, SETDB1, DNMT1 and AURKB. In some embodiments, the protein is MSK2, where reduced levels relative to a normal control is indicative of poor embryo quality, i.e. a higher probability of aneuploid development.

In other embodiments, an embryo or a population of embryos tested as having a high probability of developing aneuploidy by the methods of the invention is cultured in medium supplemented with growth factors to correct development. In some such embodiments the medium is supplemented with growth factors normally secreted by the supportive cumulus cells, which factors may be selected from BDNF, IGF-I, estradiol, GDNF, leptin and FGF2, where the medium may comprise an effective dose of one or more, two or more, three or more, up to all six of the growth factors. An alternative set of growth factors comprises BDNF, IGF-I, GDNF, EGF, GM-CSF and FGF2. Supplementation with such growth factors can improve in vitro fertilization outcomes by increasing the number of oocytes available for fertilization, reducing the inadvertent transfer of embryos with poor or variable developmental potential as well as avoiding the long-term implications of epigenetic damage in IVF embryos exposed to prolonged culture.

In one aspect, immature human oocytes are obtained from hormone-stimulated patients and matured in vitro with ovarian paracrine/autocrine factors based on the embryo requirements after analysis of altered expression of genes associated with epigenetic regulation of gene expression. In other aspects, dormant follicles are recruited from the ovary and programmed in vitro to produce oocytes assessed for quality by analysis of altered expression of genes associated with DNA methylation or histone modifications. The oocytes may also be derived from other sources, such as pluripotent stem cells differentiated in vitro into germ cells and matured into human oocytes. The developmental potential of the oocytes is determined by evaluation of expression of genes associated with DNA methylation and histone modifications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A-D. Association between mitosis, aneuploidy and the expression of epigenetic regulators in human embryos. (A) Human zygotes were cultured until the four-cell stage and previously identified cell cycle parameters predictive of blastocyst formation and ploidy status were measured by time-lapse image analysis. Embryos with abnormal parameter timing and micronuclei exhibited low MSK2 expression, whereas high MSK2 expression was observed in embryos with intact primary nuclei and normal parameter timing. (B) A lack of both H3-S10P and H3-S28P, two of the histone modifications that MSK2 mediates, was also observed in embryos with micronuclei in contrast to elevated H4-K16 acetyl, which has been shown to be involved in DNA repair and apoptosis. (C) Gene expression analysis of cleavage-stage human embryos determined to be euploid or aneuploid by A-CGH. Note the high levels of expression of both MSK2 isoforms, DNMT1, AURKA and AURKB, but not MSK1 in euploid embryos (n=13) compared with aneuploidy embryos (n=20). Grey squares indicate no expression, whereas blue, white and red squares correspond to low, medium and high expression, respectively. (D) Comparison of DNMT and histone-modifying enzyme expression in fertile, infertile and GFC-treated blastocysts (n=6-8 embryos from each group) by Q-PCR demonstrates that growth factor supplementation can partially restore the expression of epigenetic regulators to levels observed in embryos from fertile patients and beginning at the eight-cell stage of development FIG. 7. Summary model of epigenetic regulation during pre-implantation development. Embryonic development was monitored in both mouse and human embryos by imaging analysis from the zygote to the blastocyst stage. While no common DNMT expression pattern was detected, we did observe similar gene expression profiles for ATF2, KAT5, MSK2, PRMT5 and SETDB1 between mouse and human embryos, which was determined to be due, in part, to differences in expression at the single cell level. We also observed differences in the sub-compartmentalization of particular histone modifications between the two species; in humans this occurred at the 4- to 8-cell stage, while mice exhibited differential blastomere expression beginning at the morula stage. The function of the histone-modifying enzyme, Msk2, was further assessed by morpholino technologies and determined to induce micronuclei formation, embryo arrest and eventual blastomere lysis at the 3- to 8-cell stage. Correlations to human embryonic development were made by observing low Msk2 expression in human embryos with micronuclei and aberrant mitotic divisions. Based on the restoration of epigenetic regulator expression in infertile patient embryos incubated with a growth factor cocktail (GFC), we also suggest the clinical value of GFC addition to those embryos with abnormal cell cycle parameters.

DETAILED DESCRIPTION OF THE PREFERRED EMBODIMENT

Figure 1:
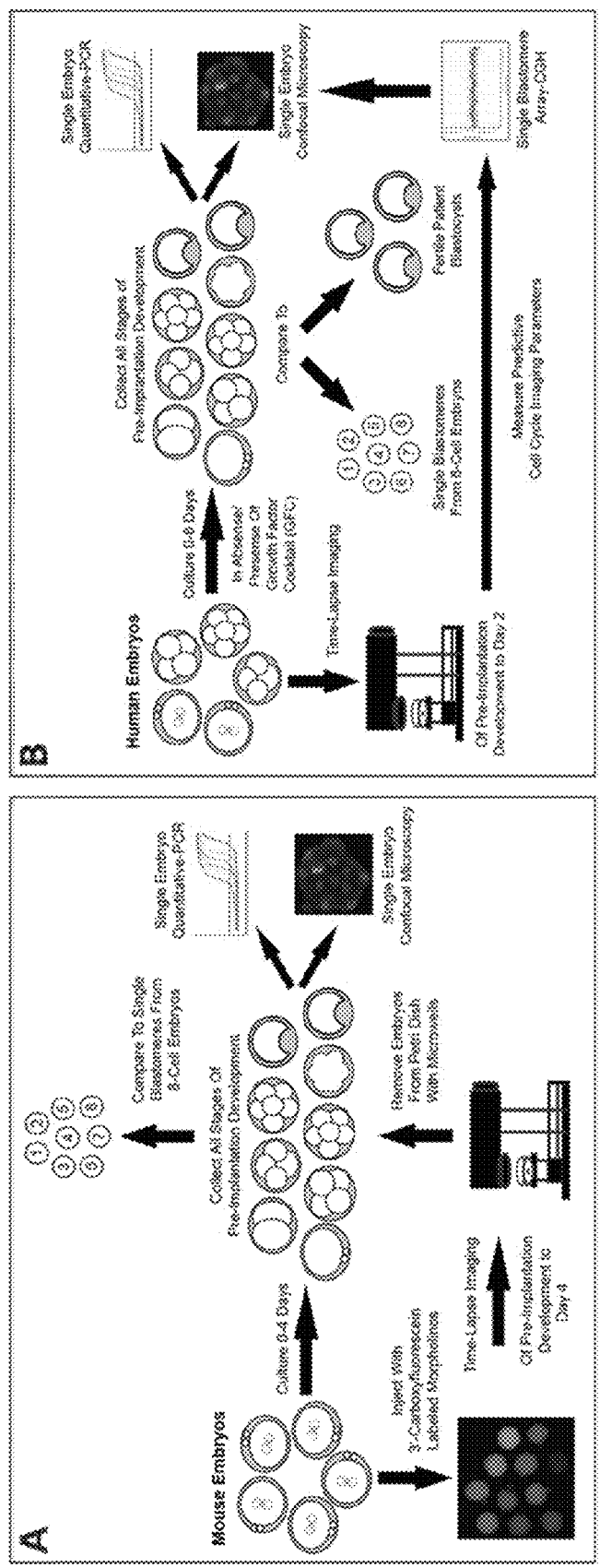
FIG. 1. Experimental design of mouse and human embryo experiments in this study. (A) Non-injected mouse zygotes were cultured up to 4 days and all stages of pre-implantation development were collected for single embryo Quantitative-PCR (Q-PCR) or confocal microscopy. Similar Q-PCR analysis was also performed on single blastomeres from 8-cell mouse embryos on Day 3. Functional analysis of a particular epigenetic regulator was accomplished by injecting with 3'-carboxyfluorescein labeled morpholinos and embryo development monitored by time-lapse imaging for comparison to non-injected embryos by Q-PCR and confocal microscopy. (B) Similar human embryo experiments were performed in the absence of presence of a growth factor cocktail (GFC) up to 6 days of culture with additional Q-PCR comparison to fertile patient blastocysts and functional assessment of human embryonic development via previously identified cell cycle parameters predictive of blastocyst formation and aneuploidy generation. The chromosome status in single human blastomeres was evaluated by Array-Comparative Genomic Hybridization (A-CGH) for correlation to single blastomere gene expression results from the same embryo or by whole embryo confocal microscopy of micronuclei formation.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods are provided for predicting the prediction of blastocyst quality of a human embryo in vitro. Prior to implantation of an embryo, e.g. beginning at the 4- to 8-cell stage, altered expression of proteins associated with epigenetic regulators of gene expression, including DNA methylation and histone modification, or mRNAs encoding such proteins, are indicative of the developmental quality potential of the embryo. Developmental quality includes the development of undesirable aneuploidy at the blastocyst stage. Analysis of epigenetic regulators of gene expression provides a means for prediction of blastocyst quality, and is useful in embryo selection for implantation; allowing selection of embryos for transfer with a greater potential for euploidy.

In some embodiments of the invention, a cell of a human embryo, usually a cell from at least the 4 cell stage and prior to the blastocyst stage, is analyzed for the presence of a protein or mRNA associated with epigenetic regulation of gene expression, where altered levels of the protein or corresponding mRNA are indicative of the embryo quality. In some embodiments, following analysis, an embryo is selected, or not selected, for transfer based on the assessment of quality. In some embodiments, the protein associated with epigenetic regulation of gene expression is one or more of ATF2, KAT5, MSK2, PRMT5, SETDB1, DNMT1 and AURKB. In some embodiments, the protein is MSK2, where reduced levels relative to a normal control is indicative of poor embryo quality, i.e. a higher probability of aneuploid development.

Growing embryos, typically between 1 to 30 per dish, are analyzed for the presence of a protein or mRNA associated with epigenetic regulation of gene expression. In some embodiments, a single cell is obtained from an embryo. In other embodiments, one or more embryos in a population are analyzed. In some embodiments, following assessment for the presence of a protein or mRNA associated with epigenetic regulation of gene expression, the embryo or population of embryos is provided with a culture medium supplemented with suitable growth factors to improve the probability of euploid development.

Embryos can be removed from the culture collected as either single embryos or single cells (blastomeres) for gene expression analysis, depending on their state in culture at the time of collection. Each plate may contains a mixture of normal and abnormal embryos—the embryos that reached the expected developmental stage at the time of harvest are considered normal, whereas those that arrested at earlier developmental stages or fragmented extensively are labelled as abnormal. Gene expression analysis can be performed with high throughput real-time quantitative PCR. Other methods of gene expression analysis may be used, such as microarrays.

The standard practice in IVF clinics is to transfer at days 3-5. Some clinics choose to culture embryos to the blastocyst stage (day-5), since blastocyst transfer has up to double the implantation rates compared to day-3 transfer. However, many clinics avoid prolonged culture due to potential risk of epigenetic disorders. The gene expression parameters can be used to predict embryo viability. This can allow for the transfer or cryo-preservation of embryos earlier than is typically practiced and before the embryos undergo significant changes in their molecular programs.

In order to increase pregnancy rates, clinicians often transfer multiple embryos into patients, potentially resulting in multiple pregnancies that pose health risks to both the mother and fetuses. In order to determine the optimal number of embryos to transfer, which is specific to each patient, the embryo viability assessment can be combined with other parameters related to patient characteristics (age), IVF cycle characteristics (fertilization rate), and embryo cohort parameters (total number of embryos), for example. A comprehensive analysis that includes an accurate prediction of embryo viability, combined with patient-specific parameters, can potentially maximize pregnancy rates while reducing the risk of multiples.

In some embodiments, the protein associated with epigenetic regulation of gene expression is one or more of ATF2, KAT5, MSK2, PRMT5, SETDB1, DNMT1 and AURKB. In some embodiments, the epigenetic regulator of gene expression is MSK2, which refers to the protein mitogen- and stress-activated protein kinase-2 (MSK2), and has the HGNC Approved Gene Symbol: RPS6KA4. The genetic sequence may be accessed at Genbank, NM_003942.2 and NM_001006944.1. MSK2 is an AGC kinase of the RSK family. It phosphorylates histone H3 and HMG-14 in response to growth factors and cellular stress.

Expression levels are obtained by analysis of an embryo or a blastomere from an embryo. A sample that is collected may be freshly assayed or it may be stored and assayed at a later time. If the latter, the sample may be stored by any means known in the art to be appropriate in view of the method chosen for assaying gene expression, discussed further below. For example the sample may freshly cryopreserved, that is, cryopreserved without impregnation with fixative, e.g. at 4° C., at −20° C., at −60° C., at −80° C., or under liquid nitrogen.

The expression levels of the genes may be measured by polynucleotide, i.e. mRNA, levels or at protein levels. Exemplary methods known in the art for measuring mRNA expression levels in a sample include hybridization-based methods, e.g. northern blotting and in situ hybridization (Parker & Barnes, Methods in Molecular Biology 106:247-283 (1999)), RNAse protection assays (Hod, Biotechniques 13:852-854 (1992)), PCR-based methods (e.g. reverse transcription PCR (RT-PCR) (Weis et al., Trends in Genetics 8:263-264 (1992)), and antibody-based methods, e.g. immunoassays, e.g., enzyme-linked immunosorbent assays (ELISAs), immunohistochemistry, and flow cytometry (FACS).

For measuring mRNA levels, the starting material is typically total RNA or poly A+RNA. A variety of different manners of measuring mRNA levels are known in the art, e.g. as employed in the field of differential gene expression analysis. In a preferred embodiment, methods for quantitating the level of one or more nucleic acids in a sample are employed based on amplification protocols, e.g., Polymerase Chain Reaction (PCR)-based assays, including quantitative PCR, reverse-transcription PCR (RT-PCR), real-time PCR, and the like, e.g. TaqMan® RT-PCR, EvaGreen Primers®, MassARRAY® System, BeadArray® technology, and Luminex technology; and those that rely upon hybridization of probes to filters, e.g. Northern blotting and in situ hybridization.

An alternative protocol for measuring mRNA levels is array-based gene expression profiling. Such protocols are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

For measuring protein levels, the amount or level of one or more proteins/polypeptides in the sample is determined, e.g., the protein/polypeptide encoded by the gene of interest. In such cases, any convenient protocol for evaluating protein levels may be employed wherein the level of one or more proteins in the assayed sample is determined.

While a variety of different manners of assaying for protein levels are known in the art, one representative and convenient type of protocol for assaying protein levels is ELISA. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Such conditions include diluting the sample with diluents such as BSA or bovine gamma globulin (BGG) in phosphate buffered saline (PBS)/Tween or PBS/Triton-X 100, which also tend to assist in the reduction of nonspecific background, and allowing the sample to incubate for about 2-4 hrs at temperatures on the order of about 25°-27° C. (although other temperatures may be used). Following incubation, the antisera-contacted surface is washed so as to remove non-immunocomplexed material. An exemplary washing procedure includes washing with a solution such as PBS/Tween, PBS/Triton-X 100, or borate buffer. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. For example, a urease or peroxidase-conjugated anti-human IgG may be employed, for a period of time and under conditions which favor the development of immunocomplex formation (e.g., incubation for 2 hr at room temperature in a PBS-containing solution such as PBS/Tween). After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzthiazoline)-6-sulfonic acid (ABTS) and H2O2, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatograpic column or filter with a wash solution or solvent.

Alternatively, non-ELISA based-methods for measuring the levels of one or more proteins in a sample may be employed. Representative examples include but are not limited to mass spectrometry, proteomic arrays, xMAP™ microsphere technology, western blotting, immunohistochemistry, and flow cytometry. In, for example, flow cytometry methods, the quantitative level of gene products of one or more TGS genes are detected on cells in a cell suspension by lasers. As with ELISAs and immunohistochemistry, antibodies (e.g., monoclonal antibodies) that specifically bind the TGS polypeptides are used in such methods.

The resultant data provides information regarding expression for each of the genes that have been probed, wherein the expression information is in terms of whether or not the gene is expressed and, typically, at what level, and wherein the expression data may be both qualitative and quantitative.

Once the expression level of the genes has been determined, the measurement(s) may be analyzed in any of a number of ways to obtain an expression representation. For example, an expression profile may be the normalized expression level of the genes in a patient sample. An expression profile may be generated by any of a number of methods known in the art. For example, the expression level of each gene may be $log_2$ transformed and normalized relative to the expression of a selected housekeeping gene, e.g. ABL1, GAPDH, or PGK1, or relative to the signal across a whole microarray, etc.

In some embodiments, an embryo or a population of embryos tested as having a high probability of developing aneuploidy by the methods of the invention is cultured in medium supplemented with growth factors to correct development. In some such embodiments the medium is supplemented with growth factors normally secreted by the supportive cumulus cells, which factors may be selected from BDNF, IGF-I, estradiol, GDNF, leptin and FGF2, where the medium may comprise an effective dose of one or more, two or more, three or more, up to all six of the growth factors. An alternative set of growth factors comprises BDNF, IGF-I, GDNF, EGF, GM-CSF and FGF2. Supplementation with such growth factors can improve in vitro fertilization outcomes by increasing the number of oocytes available for fertilization, reducing the inadvertent transfer of embryos with poor or variable developmental potential as well as avoiding the long-term implications of epigenetic damage in IVF embryos exposed to prolonged culture.

An effective dose of one or more, or all of the following growth factors can be supplemented into the medium: BDNF, IGF-I, estradiol, GDNF, leptin, FGF2, EGF, GM-CSF and FGF2.

A collected oocyte is fertilized with a sperm cell or fused with a donor nucleus and activated. Prior to, during, or following such activation the oocyte or preimplantation cell (e.g., preimplantation embryo) is cultured in a suitable growth culture medium, which facilitates the development of the resultant cell into a blastocyst. Suitable media are well known in the art and include but are not limited to one or more of: fetal calf serum (FCS), Tissue Culture Medium (TCM), Tyrodes-Albumin-Lactate-Pyruvate (TALP), Dulbecco's Phosphate Buffered Saline (PBS), as well as Eagle's and Whitten's media and the like. The medium may also include serum from one or more additional organisms. Additional media of interest are: CR1, which is disclosed in U.S. Pat. No. 5,096,822, and G1.2 and G2.2 media, which are disclosed in Gardner et al., Fertil. Steril. 69:84 (1998); both of which are incorporated herein in their entirety by reference.

Prior to contact with a viable sperm sample the isolated oocyte may be preserved in a media (for instance, a fluid or culture media) containing one or more of the supplemental growth factors to further enhance oocyte maturation prior to fertilization. Suitable maturation media include growth factors combined with one or more of: HEPES buffered hamster embryo culture medium (HECM), tissue culture medium (TCM), fetal calf serum, or the like. See Seshagine et al, Biol. Reprod., 40, 544-606, 1989; incorporated in its entirety by reference herein. Once suitably matured the sperm is then contacted with the ovum (for example at a ratio of about 75,000:1) in the fluid media (e.g., fluid media containing supplementary growth factors).

After fertilization has taken place (typically about 18 hours after incubation of the ovum with the sperm) the fertilized cell (e.g., a zygote) is then passed to another specialized growth media (for instance, a media in the absence of cumulus cells), which media, in certain embodiments, also includes one or more of the supplemental growth factors listed herein. In this manner the growth factors may be added in addition to or as a replacement for follicular cells, which would otherwise produce such factors. The zygote cell is then incubated in the growth medium until the fertilized cell has reached the 6 to 8 cell stage (e.g., has become an embryo). The time frame required for the zygote to mature to the 6 to 8 cell stage will vary but is typically between one to three days (e.g., about 48 hours). At this point the (e.g., at about 3 days) the embryo may be transferred (e.g., implanted) into a recipients uterus, for instance, via a thin, plastic catheter, which passes through the vagina and cervix.

Alternatively, if desired, an embryo at the 6 to 8 cell stage may be transferred to an extended growth culture medium for further development prior to implantation. The embryo may be cultured until deemed suitable for implantation. Typically, if cultured in this manner, the embryo is implanted once it has reached the blastocyst stage of development. Prior to and after implantation into a recipient, progesterone is typically administered to the recipient so as to prepare and sustain the uterus lining for implantation.

Although the above description was set forth with respect to several steps involved in the in vitro fertilization process it is to be understood that the order of the steps and/or the manner in which they are performed may vary dependent upon the specific protocol used. Accordingly, the order and nature of the steps detailed herein may vary without departing from the nature of the invention. For instance, more than one ovum may be collected, contacted with sperm in a BDNF containing media, and implanted into a suitable recipient.

EXPERIMENTAL

Example 1

Implications of Differential Epigenetic Expression Patterns in Mouse and Human Embryonic Blastomeres The importance of proper epigenetic regulation during pre-implantation development remains largely unknown. Here, we compared expression of key mediators of DNA methylation and histone modifications between mouse and human embryos, embryos from fertile and infertile couples, and following growth factor supplementation. We observed that while mouse embryos exhibited sub-compartmentalization of certain histone modifications between morula and blastocyst stages, differential histone modification expression was detected earlier in human embryos at the 4-8-cell stage. Likewise, differences were also observed between embryos from fertile and infertile couples and in response to growth factor supplementation. Finally, we demonstrate by time-lapse imaging that reduced expression of the histone-modifying enzyme, Msk2, resulted in embryo arrest at the cleavage-stage and was associated with the generation of aneuploidy. These data document epigenetic expression patterns between the mouse and human, in embryos obtained from fertile and infertile patients, and suggest functional roles for particular epigenetic factors during pre-implantation development.

In this study, we examine the timing and developmental stage of epigenetic regulator expression in the mouse and human. We compare expression of key regulators of DNA methylation and histone modifications between the different stages of mouse and human pre-implantation development, between embryos from fertile and infertile couples, and following addition of growth media. We then assess function via reduction in expression of a particular epigenetic regulator implicated in both mouse and human pre-implantation development. Human embryos were obtained from a unique set that were cryopreserved at the 1-cell stage prior to assessment of quality and thus, likely to be representative of "fresh" embryos from conception cycles, which have been shown to have similar potential for successful development, implantation, pregnancy and delivery as previously described (EI-Toukhy et al. (2003) Hum Reprod 18, 1313-1318).

Differential DNMT and Histone-Modifying Enzyme mRNA Expression Patterns in Mouse and Human Embryos.

Figure 2:
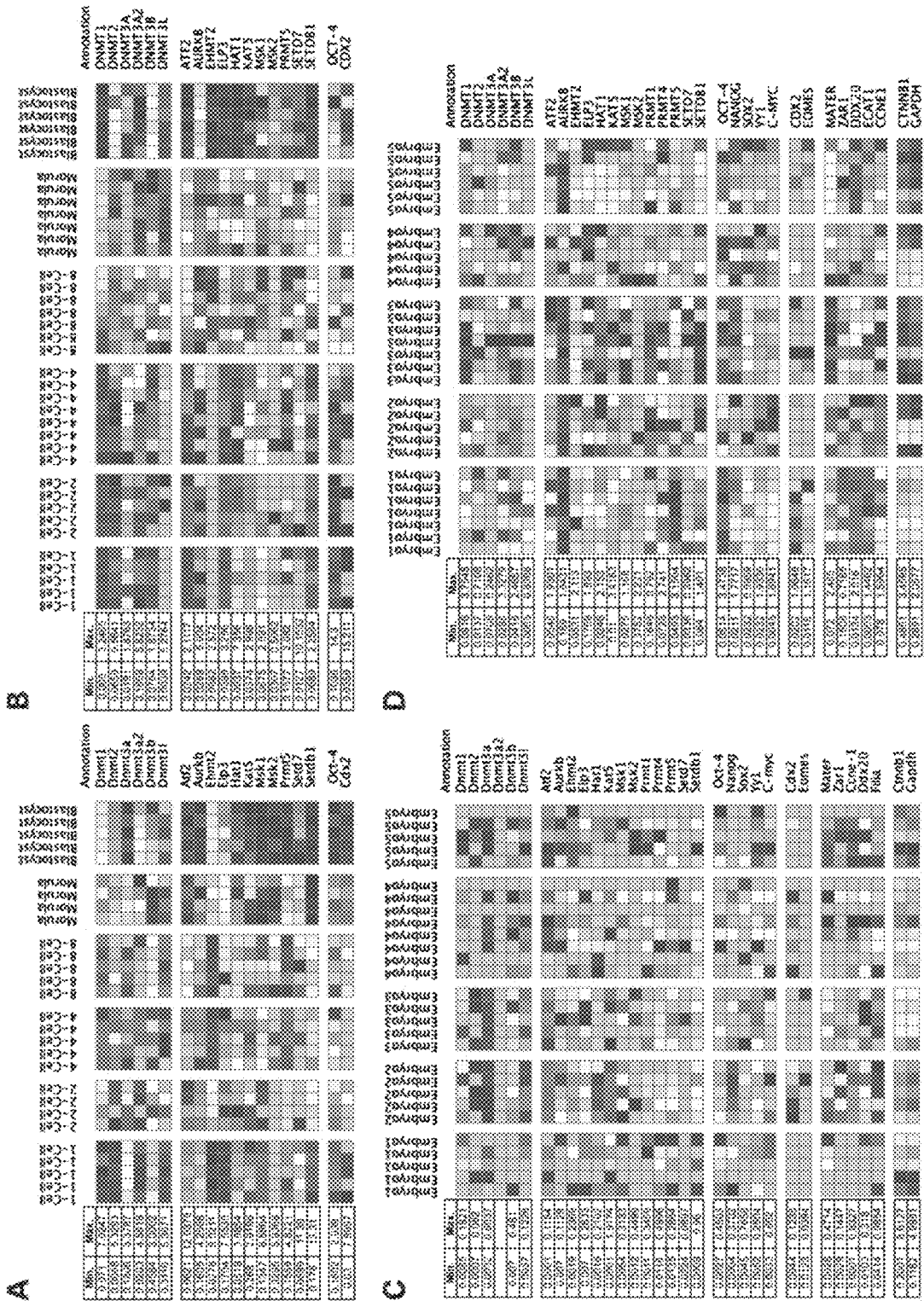
FIG. 2. Epigenetic regulator gene expression in single mouse and human embryos and blastomeres. The expression of DNA methyltransferases (DNMTs), histone-modifying enzymes, OCT-4 and CDX2 was analyzed in (A) mouse and (B) human embryos throughout pre-implantation development by microfluidic Quantitative-PCR (Q-PCR). Cycle threshold (Ct) values were normalized to the most stable housekeeping genes and graphed for comparison between the two species. Similar Q-PCR analysis of DNMTs, histone-modifying enzymes and maternal effect, zygotic activation, pluripotency and housekeeping genes as well as cell lineage markers in individual blastomeres from Day 3 (C) mouse and (D) human embryos was performed at approximately the 8-cell stage. Gray squares represent no gene expression.
Figure 8:
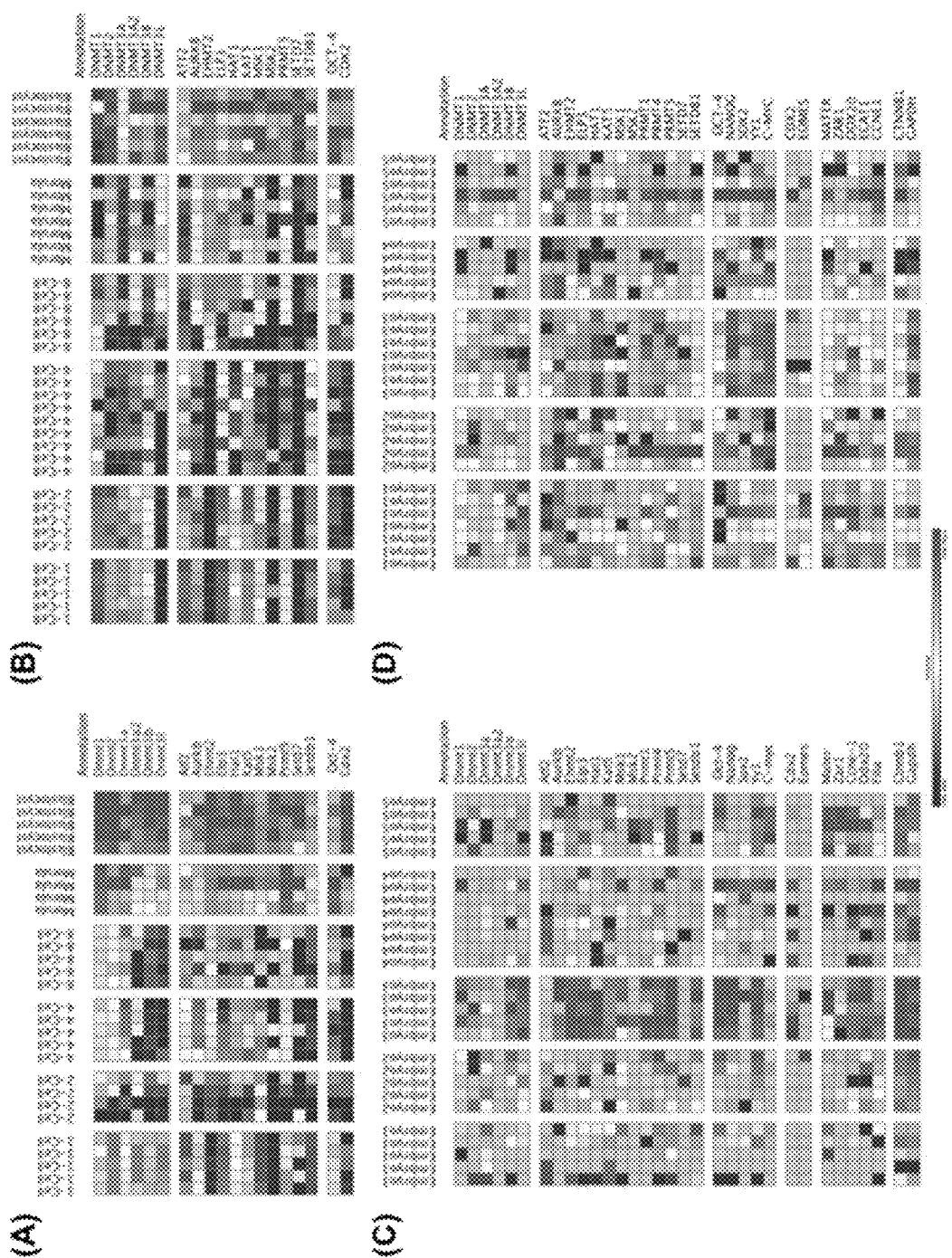
FIG. 8A-8D Non-normalized expression of epigenetic regulators in single mouse and human embryos and blastomeres. The expression of DNA methyltransferases (DNMTs), histone modifying enzymes, OCT-4 and CDX2 was analyzed in individual (a) mouse and (b) human embryos from the zygote to the blastocyst stage by microfluidic quantitative RT-PCR (Q-PCR). Non-normalized cycle threshold (Ct) values were graphed to demonstrate increased expression of numerous epigenetic regulators as cell number increases at the morula and/or blastocyst stage. Similar Q-PCR analysis of DNMTs, histone modifying enzymes and maternal effect, zygotic activation, pluripotency and housekeeping genes as well as cell lineage markers in single blastomeres from Day 3 (c) mouse and (d) human embryos was performed at approximately the 8-cell stage. Note the similar variation in single cell gene expression in blastomeres from the same embryo between mouse and human. Grey squares indicate no expression, whereas blue, white and red squares correspond to low, medium and high expression, respectively.

We first examined which DNMTs were associated with different stages of pre-implantation development in mouse and human embryos (FIGS. 1A and 1B). For this purpose, we evaluated DNMT1, DNMT2, DNMT3A, DNMT3A2, DNMT3B and DNMT3L expression in individual mouse or human embryos at the 1-cell, 2-cell, 4-cell, 8-cell, morula and blastocyst stages by microfluidic Q-PCR (Table 1). As shown in FIG. 2A and FIG. 8A, some differences in DNMT expression between mouse embryos were detected beginning at the 2-cell stage when zygotic/embryonic genome activation begins in the mouse, until the 8-cell stage of development; less variation in DNMT expression patterns was observed between individual mouse 1-cell, morula and blastocysts. In human embryos, greater variation in DNMT expression was detected between individual human embryos at the cleavage stage than in the mouse and this variation occurred later in development (between the 4- to 8-cell stage, coincident with the major wave of embryonic genome activation, and the morula stage; FIG. 2B and FIG. 8B). Moreover, variation in the expression of DNMTs that function in maintenance versus de novo methylation was also observed in human pre-implantation embryos. Thus, no common DNMT expression pattern could be detected between mouse and human embryos, confirming the differences in global DNA methylation levels observed in each species.

TABLE 1

| Gene Symbol | Gene Classification | Human Assay ID | Mouse Assay ID |
| --- | --- | --- | --- |
| DNMT1 | DNA methylation | Hs00945899_m1 | Mm00599763_m1 |
| DNMT2 | DNA methylation | Hs00189402_m1 | Mm00438508_m1 |
| DNMT3A | DNA methylation | Hs00173377_m1 | Mm00432870_m1 |
| DNMT3A2 | DNA methylation | Hs00601097_m1 | Mm00463987_m1 |
| DNMT3B | DNA methylation | Hs00171876_m1 | Mm01240113_m1 |
| DNMT3L | DNA methylation | Hs00203536_m1 | Mm00457635_m1 |
| PRMT1 | Histone-modification | Hs01587651_g1 | Mm00480142_g1 |
| PRMT4 | Histone-modification | Hs00406354_m1 | Mm00491417_m1 |
| PRMT5 | Histone-modification | Hs00272020_m1 | Mm00515108_m1 |
| MSK1 | Histone modification | Hs00178054_m1 | Mm00463868_m1 |
| MSK2 | Histone modification | Hs00177670_m1 | Mm00451280_m1 |
| AURKB | Histone modification | Hs00177782_m1 | Mm01718140_m1 |
| SETD7 | Histone modification | Hs00363902_m1 | Mm00499823_m1 |
| SETDB1 | Histone modification | Hs01051024_g1 | Mm00450791_m1 |
| EHMT2 | Histone modification | Hs00198710_m1 | Mm01132261_m1 |
| ELP3 | Histone modification | Hs00216429_m1 | Mm00804536_m1 |
| KAT5 | Histone modification | Hs00197310_m1 | Mm00724374_m1 |
| ATF2 | Histone modification | Hs00153179_m1 | Mm00833804_g1 |
| HAT1 | Histone modification | Hs00186320_m1 | Mm00509140_m1 |
| OCT4 | Pluripotency | Hs03005111_g1 | Mm00658129_gH |
| NANOG | Pluripotency | Hs02387400_g1 | Mm02384860_g1 |
| SOX2 | Pluripotency | Hs00602736_s1 | Mm00488369_s1 |
| YY1 | Pluripotency | Hs00231533_m1 | Mm00456392_m1 |
| C-MYC | Pluripotency | Hs00153408_m1 | Mm00432449_m1 |
| CDX2 | Trophoectoderm | Hs00230919_m1 | Mm00432449_m1 |
| EOMES | Trophoectoderm | Hs00172872_m1 | Mm01351984_m1 |
| MATER | Maternal effect | Hs00411266_m1 | Mm00488691_m1 |
| ZAR1 | Maternal effect | Hs00601843_m1 | Mm00558078_m1 |
| DDX-20 | Zygotic activation | Hs00200516_m1 | Mm00553372_m1 |
| Filia | Zygotic activation | | Mm00804161_g1 |
| ECAT1 | Ortholog of Filia | Hs01584167_g1 | |
| GAPDH | Housekeeping | 4352934E | Mm99999915_g1 |
| CTNNB1 | Housekeeping | Hs00170025_m1 | Mm01350394_m1 |

Human and mouse probes for gene expression analysis in single embryos and individual blastomeres. The gene symbol, classification and human and/or mouse assay identification (ID) number of probes used for Quantitative-PCR analysis in the study. Note that the assays were designed to span exons in order to distinguish between cDNA and genomic DNA products.

We next examined the expression of the enzymes that mediate particular histone modifications in both mouse and human pre-implantation embryos (FIGS. 1A and 1B). To accomplish this, we focused our attention on histone-modifying enzymes that are involved in the phosphorylation of serine residues [Aurora B Kinase (AURKB), Mitogen- and stress-activated protein kinase 1 and 2 (MSK1 and MSK2], acetylation of lysine residues, Activating transcription factor 2 (ATF2), Elongator complex protein 3 (ELP3), Histone acetyltransferase 1 (HAT1), and K (lysine) acetyltransferase 5 (KAT5), and the methylation of either lysine residues, Euchromatic histone-lysine N-methyltransferase 2 (EHMT2), SET domain containing 7 (SETD7) and SET domain bifurcated 1 (SETDB1) or arginine residues, Protein arginine methyltransferase 5 (PRMT5).

Analogous to DNMT expression patterns, the levels and timing of expression of most histone-modifying enzymes differed between mouse and human embryos (FIG. 2A, 2B and FIG. 8A, 8B). Indeed, only ATF2, KAT5, MSK2, PRMT5 and SETDB1 were similarly expressed in mouse and human pre-implantation embryos. Moreover, the greatest differences in histone-modifying enzyme expression were detected in human embryos between the 4- to 8-cell and morula stages (FIG. 2B and FIG. 8B). The variability in both DNMT and histone-modifying enzyme expression was correlated with differences in the expression of the cell lineage markers, Octamer-binding Transcription Factor-4 (OCT-4) and Caudal-Type Homeobox 2 (CDX2), markers that have been shown to be predictive of ICM and trophoectoderm lineage patterning (Plachta et al. (2011) Nat Cell Biol 13, 117-123; Jedrusik et al. (2008) Genes Dev 22, 2692-2706), respectively (FIG. 2A, 2B and FIG. 8A, 8B).

Single-Cell Analysis of Epigenetic Regulators in Cleavage-Stage Mouse and Human Embryos.

We next sought to evaluate epigenetic regulator expression in single blastomeres from the same embryo. For this purpose, Day 3 mouse and human embryos were disassembled to single cells at approximately the 8-cell stage, a time when the embryonic genomes of both species should be activated, and DNMT and histone-modifying enzyme expression was analyzed by microfluidic Q-PCR (FIGS. 1A and 1B). Both mouse and human blastomeres exhibited a similar degree of variation in DNMT and histone-modifying expression within the same embryo; this variation was also reflected in blastomere differences between OCT-4 and CDX-2 expression as well as other pluripotency regulators, including NANOG, SOX2, YY1 and c-MYC, and trophoectoderm markers such as EOMES (FIG. 2C, 2D and FIG. 8C, 8D).

However, differences in the expression of pluripotency, trophoectoderm and epigenetic regulators were not universal to all genes expressed at this stage of development since little or no variation was observed in the expression of the maternal-effect genes, MATER, ZAR and CCNE-1, zygotic/embryonic genome activation genes, DDX-20, Filia, ECAT1 (considered to be the ortholog of Filia (Pierre, A. et al. Genomics 90, 583-594 (2007)), or other genes such as CCNA-1 (FIG. 2C, 2D and FIG. 8C, 8D).

Analysis of Histone Modification Sub-Compartmentalization in Mouse and Human Embryos.

Figure 3:
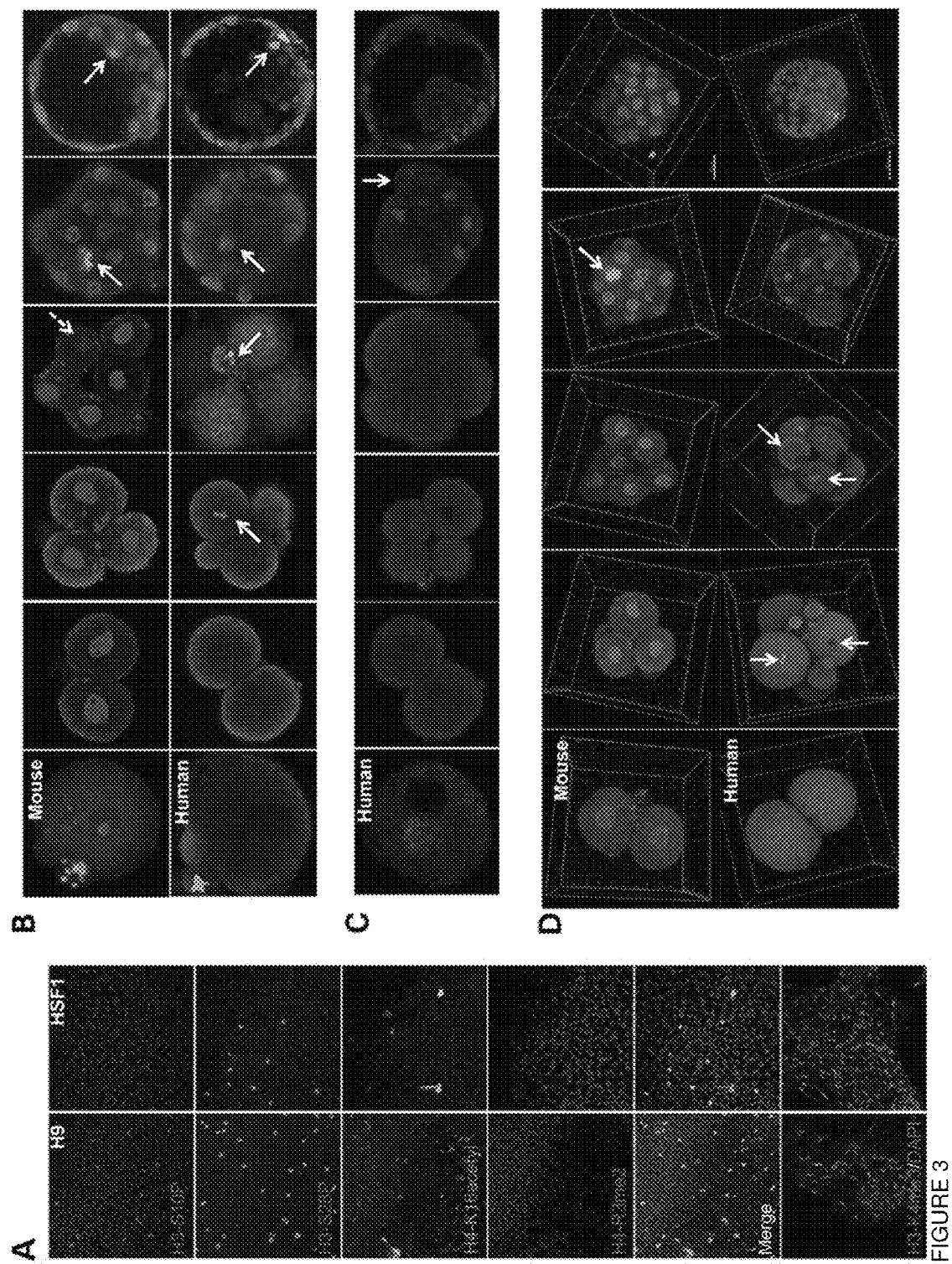
FIG. 3. Multi-channel confocal analysis of histone modifications in mouse and human embryos. (A) Undifferentiated human embryonic stem cell (hESC) lines (H9; XX and HSF1; XY) were immunostained with several different histone modification antibodies and Histone H3-S10P (blue), H3-S28P (green), H4-K16acetyl (orange), H4-R3me2 (red) were chosen for further analysis based on their expression pattern. Since Histone H4-R3me2 has been shown to be associated with both transcriptional activation and repression, the undifferentiated hESCs were also incubated with a primary antibody for Histone H3-K4me3 (red), a transcriptionally active mark, and DAPI (blue). Both H3-S10P and DAPI required use of the blue confocal channel and therefore, could not be analyzed simultaneously. (B) The expression and localization of Histone H3-S10P, H3-S28P, H4-K16acetyl and H4-R3me2 was then analyzed mouse and human embryos throughout pre-implantation development by multi-channel confocal microscopy (N=6 to 8 embryos per stage). Note the difference in developmental stage of histone modification sub-compartmentalization between mouse and human embryos (indicated by white arrows). (C) Similar confocal analysis of Histone H3-K4me3 in human embryos exhibiting positive expression in one of the pro-nuclei at the zygote stage as well as certain blastomeres beginning at the 8-cell stage. (D) 3-D modeling of histone modifications in mouse and human embryos from the 2-cell to blastocyst stage by Z-stack confocal microscopy demonstrating further evidence of differences in the timing of sub-compartmentalization between the two species.
Figure 9:
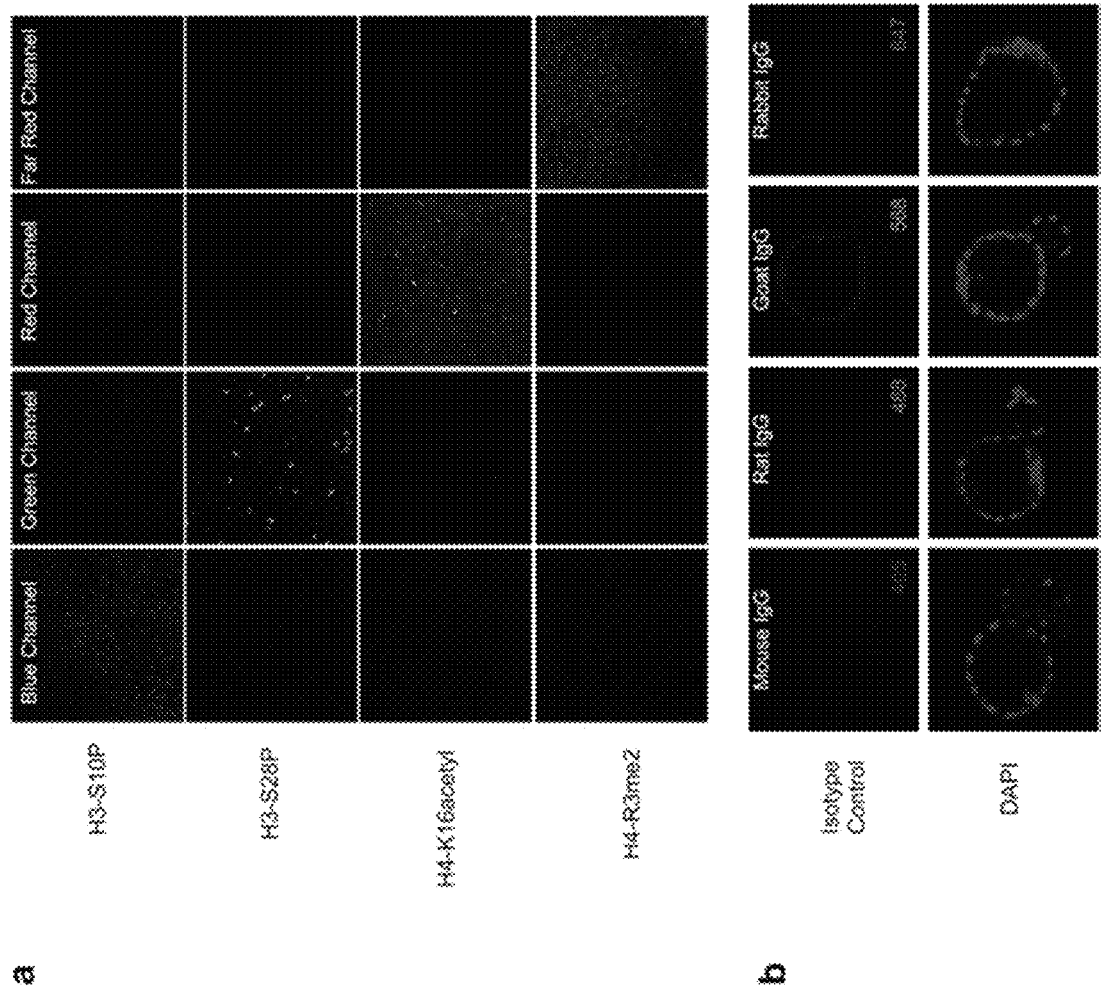
FIG. 9A-B. Assessment of immunostaining controls by confocal microscopy. (a) Undifferentiated human embryonic stem cells (H9; XX) were incubated with Histone H3-S10P (blue), H3-S28P (green), H4-K16acetyl (orange) or H4-R3me2 (red) primary antibody only followed by the appropriate 405-, 488-, 568-, or 647-labeled secondary antibody. The blue, green, red and far-red channels were visualized by confocal microscopy to eliminate the possibility of cross-contamination between the different confocal channels. (b) Mouse blastocysts were incubated with a mouse, rat, goat, or rabbit IgG isotype control antibody at similar concentrations as the corresponding histone modification antibody followed by the appropriate fluorescently-labeled secondary antibody and staining with DAPI (blue) for analysis by confocal microscopy. Note that confocal analysis of Histone-S10P was performed first before DAPI staining since the 405-labeled secondary antibody and DAPI both require the blue channel. Relatively little or no immunostaining was detected using the same confocal settings to ensure the specificity of each histone modification.

Using immunofluorescence and multi-color confocal microscopy analysis, we then assessed changes in the expression of certain histone modifications in mouse and human embryos at the protein level (FIGS. 1A and 1B). We focused our attention on the expression and localization of Histone H3 serine 10 phosphorylation (H3-S10P), H3-S28P, Histone H4 lysine 16 acetylation (H4-K16acetyl) and Histone H4 arginine 3 dimethylation (H4-R3me2) given that the mRNAs for the corresponding histone-modifying enzymes were expressed in mouse and human embryos. The expression of Histone H3 lysine 4 tri-methylation (H3-K4me3) was also evaluated since H4-R3me2 can be both a transcriptionally active and repressive mark. We validated specificity of the antibodies by immunofluorescence in the undifferentiated human embryonic stem cell (hESC) lines, H9 (XX) and HSF1 (XY) (FIG. 3A). Negative controls included single color antibody staining to discount potential interference between different confocal channels as well as isotype controls (FIGS. 9A and 9B).

We then evaluated expression and localization of histone modifications in mouse embryos and observed that each blastomere exhibited a similar epigenetic expression pattern during the early cleavage stages of development both by single frame confocal imaging (FIG. 3B and FIG. 10B) and 3-dimensional modeling of Z-stacked confocal images (FIG. 3D). However, there were differences in the level of histone modification expression between blastomeres within the same embryo, which is in accordance with previous findings (Torres-Padilla et al. Nature 445, 214-218 (2007)). As FIG. 3B and FIG. 10A demonstrate, it was not until the morula and blastocyst stages (indicated by white arrows) that sub-compartmentalization of these epigenetic factors was observed. Notably, we observed H3-K4me3 and H4-R3me2 expression in one or both of the pronuclei and H3-S28P expression in one of the polar bodies in mouse embryos at the 1-cell stage (FIG. 3B and FIG. 10A, 10C), suggesting that H3-S28P may be a marker of the first polar body since H3-S28P is associated with mitosis and the first polar body can undergo cytokinesis. Moreover, the expression of H3-S10P appeared to localize to small structures in the cytoplasm of only cleavage-stage mouse embryos, which may be explained by previous findings that histones can bind strongly to isolated mitochondria, the phosphorylation of histone H3 is associated with mitosis, and mitotic progression is closely integrated with mitochondrial dynamics.

Figure 10:
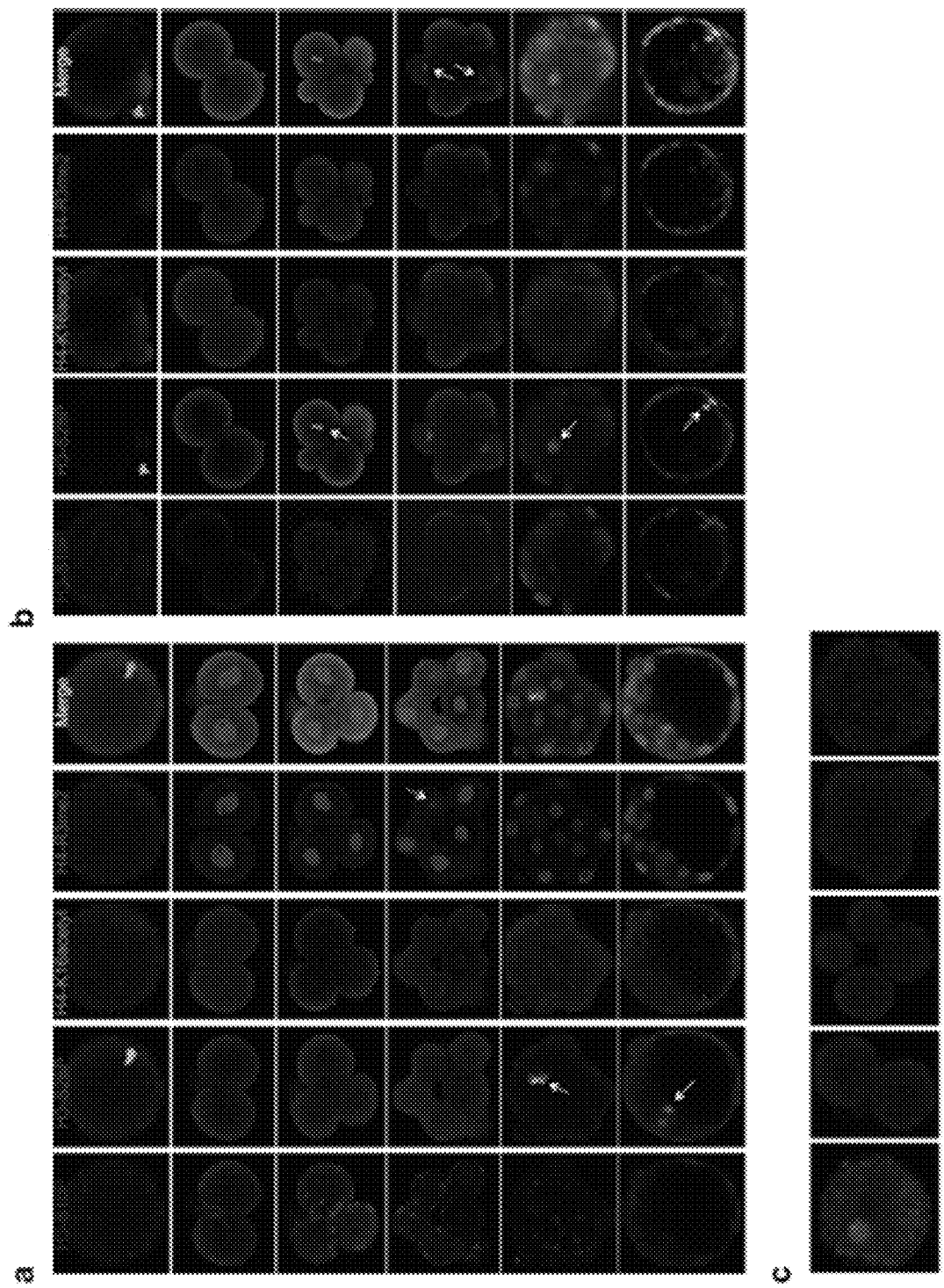
FIG. 10A-C. Single channel confocal analysis of histone modifications in mouse and human embryos. The expression and localization of Histone H3-S10P, H3-S28P, H4-K16acetyl and H4-R3me2 was analyzed in (a) mouse and (b) human embryos throughout pre-implantation development by confocal microscopy. Note the difference in developmental stage of when histone modification sub-compartmentalization, including H3-S28P, begins between blastomeres in mouse (morula to blastocyst stage) and human (4- to 8-cell stage embryos (indicated by white solid arrows). However, different levels of expression of the same histone modification such as H4-R3me2 was observed between blastomeres in mouse embryos earlier in development (shown by white dashed arrows). (c) Similar confocal analysis of Histone H3-K4me3 in mouse embryos demonstrating positive expression in one of the pro-nuclei at the zygote stage as well as certain cells at the blastocyst stage.

In contrast to mouse embryos, human embryos exhibited differential histone modification expression patterns by the 4- to 8-cell stage when analyzed by single frame confocal imaging (FIG. 3B and FIG. 10B) and 3-dimensional modeling of Z-stacked confocal images (FIG. 3D). Similar to the mouse, however, sub-compartmentalization of histone modifications was also detected in human embryos at the morula and blastocyst stages as well as within the inner cell mass (ICM) and trophoectoderm sub-populations (FIG. 3B and FIG. 10B). As shown in FIG. 3B, 3D and FIG. 10B, individual human blastomeres expressed either different histone modification marks, even in the same nucleus in certain instances, or were devoid of histone modification expression observed in other blastomeres within the same embryo (indicated by white arrows). Immunostaining of human embryos for H3-K4me3 also revealed a differential histone modification expression pattern at the 8-cell stage of human development in addition to positive signals for H3-K4me3 and H3-S28P in one of the pro-nuclei and polar bodies at the 1-cell stage, respectively (FIG. 3C and FIG. 10B).

Figure 4:
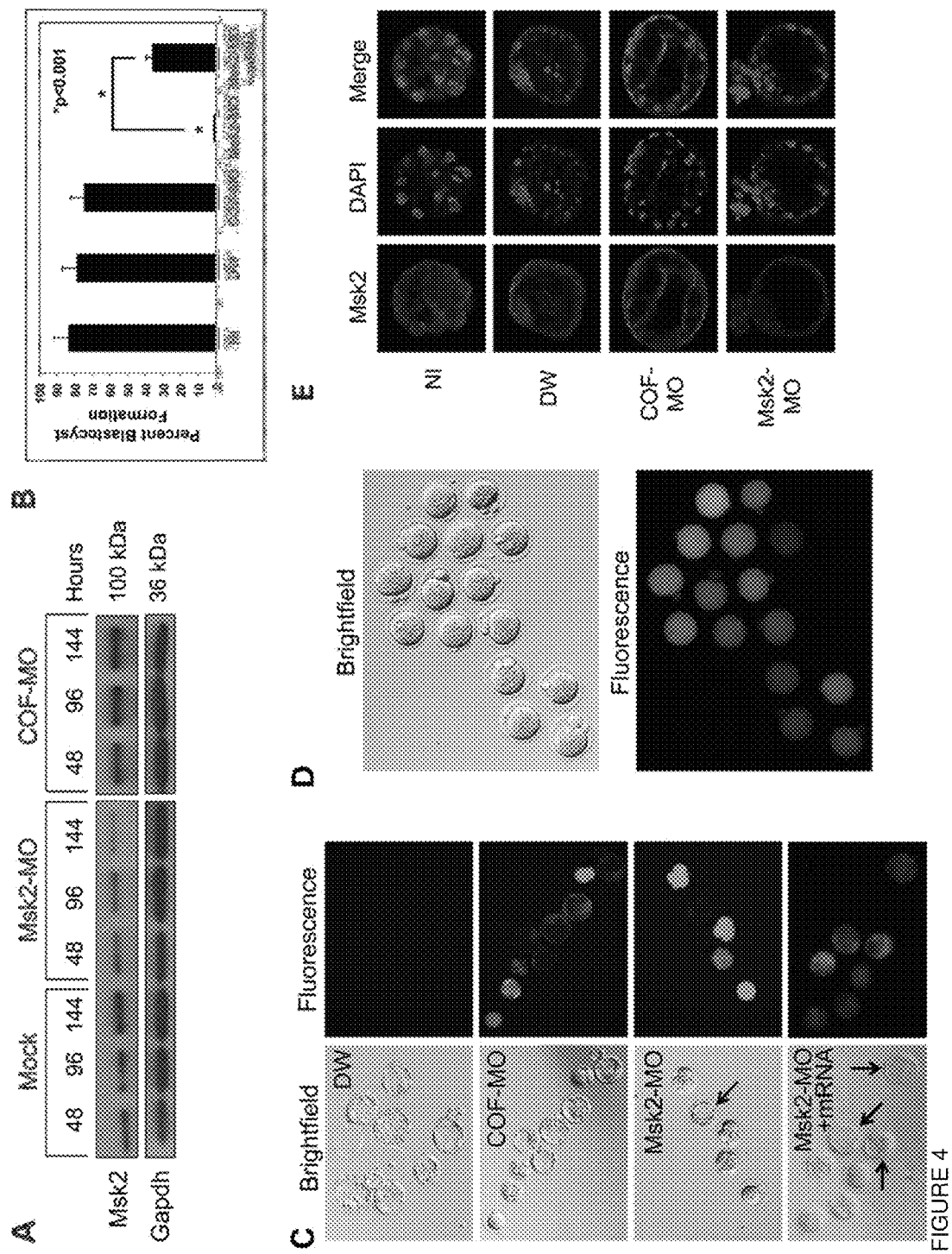
FIG. 4. Knockdown of Msk2 expression reduces blastocyst formation rates. (A) The efficiency of Msk2 knockdown was first assessed by nucleofecting undifferentiated E8.5 mouse embryonic germ cells with water (mock), Msk2 morpholino (Msk2-MO) or 3'-carboxyfluorescein-labeled standard control morpholino (COF-MO) and Msk2 expression (100 kDa) evaluated using Gapdh (36 kDa) as a loading control by Western Blot analysis 48-144 hours later. (B) Blastocyst formation rates were calculated for non-injected (NI; N=73) as well as water (DW; N=19), COF-MO (N=71) and Msk2-MO (N=73) injected mouse embryos. Graphic representation of the percentages for each experimental group, including the percent blastocyst formation following the co-injection of Msk2-MO and Msk2 mRNA (Msk2-MO+mRNA; N=33) in embryos is as shown. (C) Brightfield imaging and fluorescent microscopy of embryos in each group from one representative experiment. Note the single blastocyst observed following injection with the Msk2-MO (indicated by black arrow), (D) which may be explained by the amount of morpholino injected as revealed by slight differences in fluorescent intensities at the zygote stage. (E) Reduced Msk2 expression was detected in the single Msk2-MO injected blastocyst obtained in comparison to the other experimental groups.

In order to determine whether specific histone-modifying enzymes were implicated in the progression of pre-implantation development beyond embryonic genome activation, we microinjected morpholinos (MOs) at the 1-cell stage and monitored embryo development by time-lapse imaging (FIG. 1A). To facilitate an understanding of both mouse and human development, we initially focused our attention on the histone-modifying enzymes that were similarly expressed in both mouse and human embryos (ATF2, KAT5, MSK2, PRMT5 and SETDB1). However, ATF2, KAT5, PRMT5 and SETDB1 had multiple transcript variants, a high percentage of GC base content around the first exon and/or an atypical start codon, making MO design difficult for these histone-modifying enzymes. Given that relatively little is known about the role of serine phosphorylation in pre-implantation development and the importance of mitosis at the cleavage stage, we focused our efforts on Msk2, a mitogenic factor that has been shown to regulate the cell cycle (Vigneron, S. et al. Oncogene 29, 3566-3574 (2010)). We first sought to determine if we could specifically knockdown Msk2 expression using a MO designed to target the translation start site of Msk2. To accomplish this, E8.5 mouse embryonic germ (mEG) cells were mock transfected or transfected with either a 3'-carboxyfluorescein-labeled standard control or 3'-carboxyfluorescein-labeled Msk2 MO by nucleofection and the expression of Msk2 was evaluated by Western Blot analysis 48-144 hours later since these cells express high levels of Msk2 and Western Blot analysis of Msk2 knockdown in pre-implantation embryos would require several hundred embryos in each experimental group. In contrast to the mock transfection or control MO, the nucleofected Msk2 MO efficiently knocked down Msk2 protein expression in 8.5 mEGs (FIG. 4A).

Figure 11:
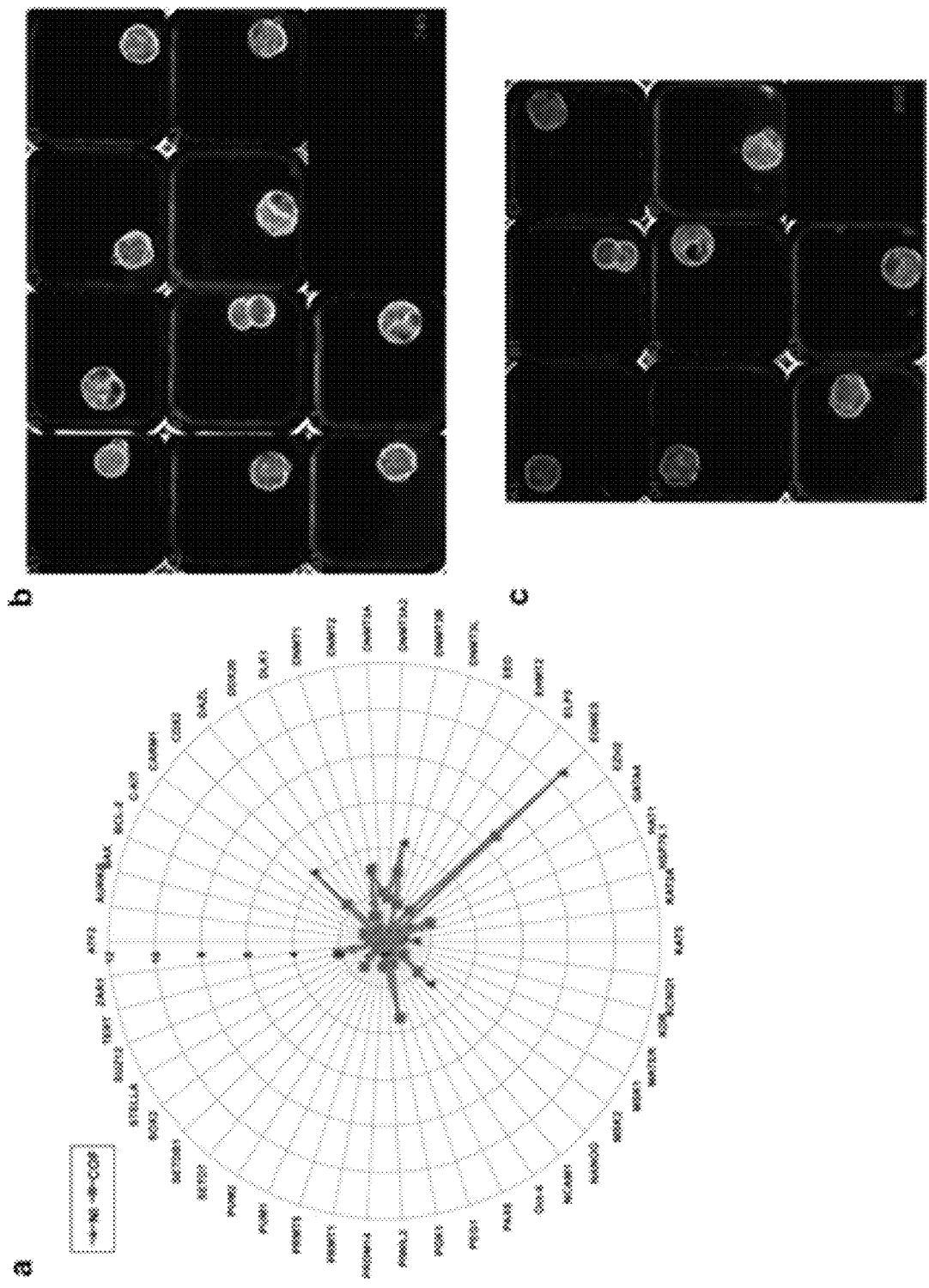
FIG. 11A-C. Developmental comparison of non-injected and 3'-carboxyfluorescein morpholino-injected mouse embryos. (a) Gene expression analysis of 50 genes from different sub-categories, including DNMTs, histone modifying enzymes, polycomb, imprinting, apoptosis, maternal effect, zygotic activation, pluripotency as well as cell lineage markers showed a difference in the expression of only two trophoblast genes, Cdx2 and Eomes, between non-injected (N=12) and 3'-carboxyfluorescein (COF) morpholino standard control-injected (N=12) mouse embryos. (b) The first time-lapse imaging frame in which blastocoel formation was detected in non-injected and (c) 3'-COF-injected mouse embryos. Note the difference in imaging frame (745 in non-injected; 898 in 3'-COF-injected embryos), which suggests that the difference in Cdx2 and Eomes expression between the two groups may be due to a delay in development (approximately 12 hours) from microinjection.
Figure 12:
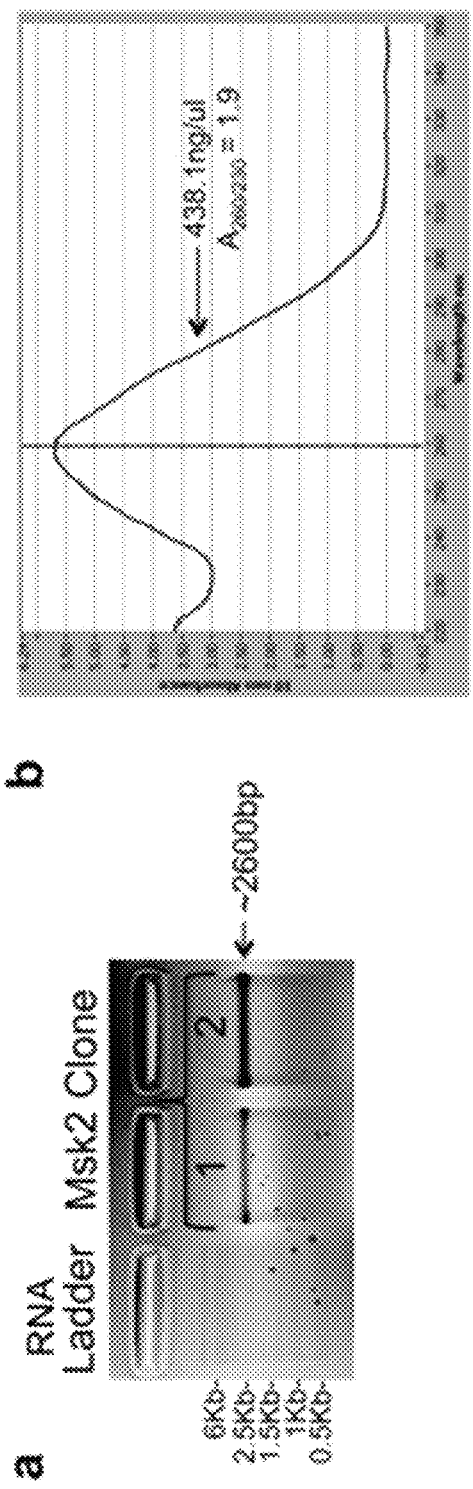
FIG. 12A-B Verification of modified Msk2 mRNA size, quantity and purity. (a) Two modified Msk2 mRNA clones were analyzed by formaldehyde agarose gel electrophoresis using an RNA ladder for size comparison. Note the approximate size of Msk2 clones, which takes into account the size (~2300 bp) of the Msk2 open reading frame (ORF) plus the 5' cap/UTR and 3' UTR/poly-A-tail (~280 bp), as well as the little or no mRNA degradation. (b) Spectrophotometer reading of Msk2 clone #1 showing the concentration and purity of the modified mRNA based on the absorbance at a wavelength of 260 nm and the $A_{260/230}$ ratio, respectively.

After we had confirmed specific Msk2-mediated knockdown, our next objective was to determine whether microinjection of the Msk2 MO using the injection of the 3'-carboxyfluorescein labeled MO as a control had any effects on pre-implantation development. Initially, we determined that both non-injected and water injected 1-cell mouse embryos exhibited similar rates of blastocyst formation at approximately 80%, while 75% blastocyst formation rates were observed in standard control injected embryos (FIGS. 4B and 4C) as demonstrated by time-lapse imaging. More importantly, when the gene expression profiles of non-injected and standard control injected blastocysts were compared, differences in the expression of only 2 out of the 50 genes tested could be detected (FIG. 11A). The two genes that were expressed at higher levels in non-injected embryos were the trophoblast markers, Cdx2 and Eomes, which may be explained by the finding that a slight delay (approximately 12 hours) in blastocyst formation was observed in control injected over non-injected embryos (FIGS. 11B and 11C; note differences in image frame number, Table 2).

cated by black arrow). This exception may be due to minor differences in the volume of MO injected into each embryo as demonstrated by the slight variation in fluorescent intensities between embryos following sequential injection (FIG. 4D). However, we observed that there was a decrease in the expression of Msk2 detected in the one Msk2-MO injected embryo that reached the blastocyst stage compared to level of Msk2 expression detected in non-injected, water or 3'-carboxyfluorescein labeled MO injected embryos (FIG. 4E).

Figure 5:
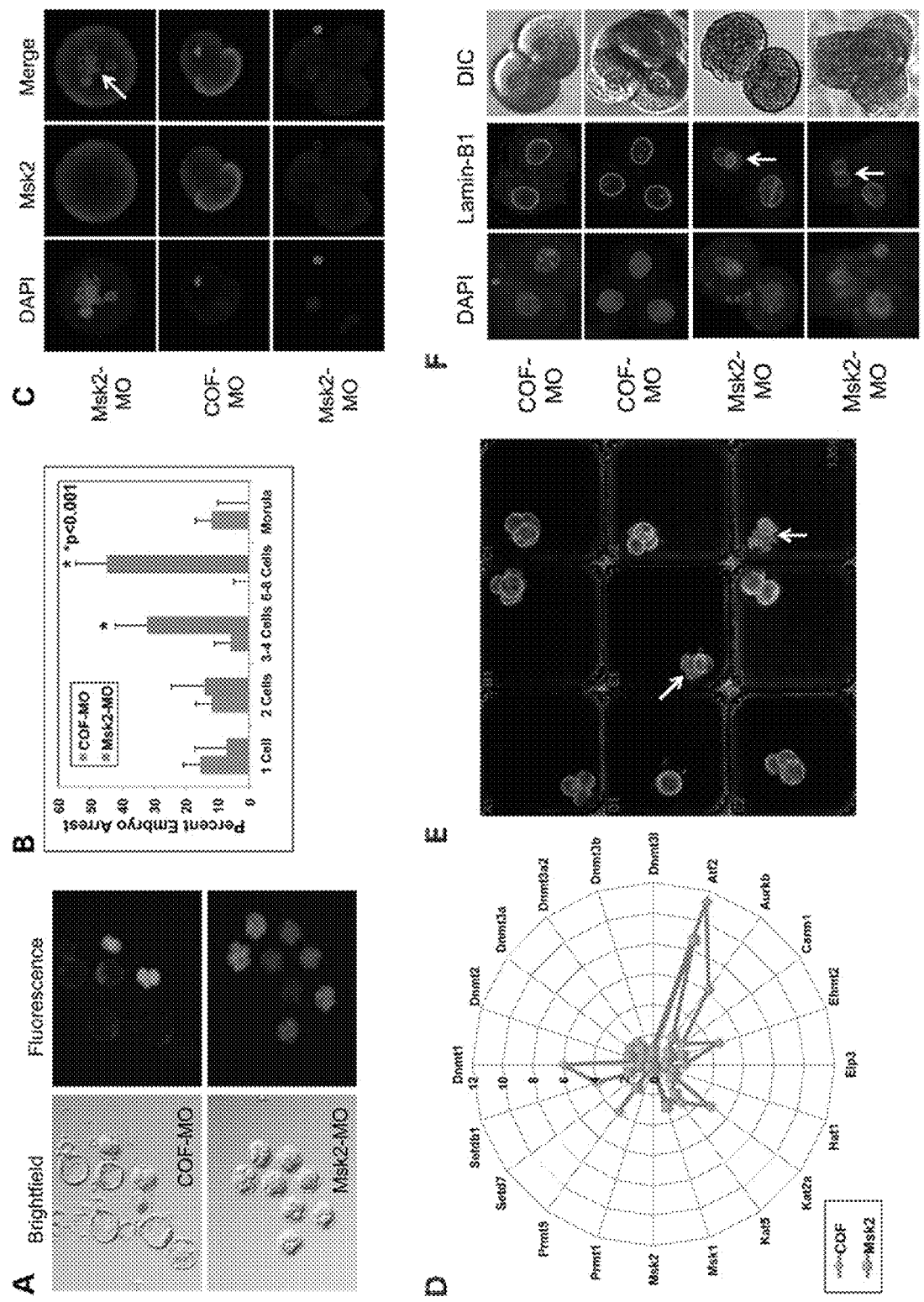
FIG. 5. Msk2 knockdown induces mitotic arrest and is associated with aneuploidy generation. (A) Brighfield imaging and fluorescent microscopy of 3'-carboxyfluorescein-labeled standard control morpholino (COF-MO) and Msk2 morpholino (Msk2-MO)-injected mouse embryos demonstrates that the Msk2-MO-mediated embryonic arrest occurs at the cleavage stage. (B) A closer examination of each developmental stage reveals a significant increase (p<0.001) in Msk2-MO-induced arrest at the 3-8 cell stage. (C) Confocal microscopy of Msk2 expression in DAPI stained embryos shows that the embryo arrest that occurred at the 1-cell stage following Msk2-MO injection is due to other reasons such as polyploidy (indicated by white arrow) and that reduced Msk2 expression is observed in Msk2-MO compared to COF-MO injected embryos. (D) Gene expression analysis of DNA methyltransferases (DNMTs) and histone-modifying enzymes in COF-MO and Msk2-MO injected embryos demonstrates that Msk2 knockdown has effects on other known mitotic regulators. (E) The last frame of an image sequence compiled into a time-lapse movie), which shows increased blastomere movement and eventual lysis resembling mitotic catastrophe in some Msk2-MO injected embryos. (F) Lamin-B1-encapsulated micronuclei are observed in Msk2-MO, but not COF-MO injected embryos stained with DAPI and imaged by DIC (N=10 embryos from each group), suggesting that mouse embryos may avoid chromosomal instability by inducing cell lysis.

Following our observation that the knockdown of Msk2 in mouse embryos significantly reduced blastocyst formation rates, we then examined the developmental timing of embryo arrest. A closer examination of each stage of pre-implantation development revealed that Msk2-medidated arrest most commonly occurred in 3- to 8-cell embryos (FIG. 5A). More specifically, arrest was observed in approximately 40% of 3-4 cell embryos and 51% of 6-8 cell embryos following injection of the Msk2-MO (p<0.001; FIG. 5B). In addition, we also determined that the few embryos that arrested at the 1-cell stage were due to other reasons such as polyploidy (FIG. 5C; upper panel; indicated by white arrows). Moreover, a decrease in Msk2 expression was observed in non-polyploid Msk2-MO injected 2-cell mouse embryos prior to arrest in comparison to 3'-carboxyfluorescein labeled MO injected embryos at a similar stage (FIG. 5C; middle and lower panels).

Finally, when we evaluated the epigenetic gene expression profiles in 3'-carboxyfluorescein labeled MO or Msk2 injected embryos, we detected differences in the expression of Dnmt1 and Aurkb, additional epigenetic regulators that have known mitotic functions (Leonhardt, H. et al. Cell 71, 865-873 (1992); Yang, F. et al. J Cell Sci 120, 4060-4070 (2007)), in Msk2-MO embryos (FIG. 5D), suggesting that Msk2 knockdown had adverse effects on other epigenetic mechanisms in developing embryos. Assessment of embryo behavior revealed that Msk2-injected embryos exhibited the

TABLE 2

|  | Non-injected (NI) | Water-injected (DW) | 3'-Carboxyfluorescein morpholino-injected (COF) | Msk2 morpholino-injected (Msk2-MO) | Msk2 morpholino + modified mRNA-injected (Msk2-MO + mRNA) |
| --- | --- | --- | --- | --- | --- |
| Number of independent experiments | 7 | 2 | 7 | 7 | 3 |
| Number of embryos reaching blastocyst stage | 61 | 15 | 55 | 1 | 12 |
| Total number of embryos | 73 | 19 | 71 | 73 | 33 |
| Percentage | 83% | 79% | 77% | 1.4% | 36% |

The number and percentage of blastocysts obtained in independent microinjection experiments. A table displaying the number of independent experiments performed, the number of embryos that reached the blastocyst stage out of the total number of embryos with the corresponding percentage in the different microinjection groups. Note that only 1 embryo became a blastocyst in the Msk2-morpholino injected (Msk2-MO) group and this Msk2-induced embryo arrest was partially rescued by co-injecting with a similar concentration (20 ng/ul) of modified Msk2 mRNA (Msk2-MO + mRNA).

Once we had determined that the 3'-carboxyfluorescein labeled standard control had little or no effect on pre-implantation development, we then evaluated the effects of Msk2 specific knockdown by comparing similar concentrations of Msk2 and standard control injected MOs. As FIG. 4B indicates, only 1.4% blastocyst formation rates were observed with the Msk2 injected 1-cell mouse embryos and co-injection with a modified Msk2 mRNA partially rescued this effect by increasing blastocyst development to approximately 38% (p<0.001). Notably, of the approximately 75 mouse embryos injected with the Msk2 MO, only a single embryo developed to the blastocyst stage (FIG. 4C; indiunusual phenotype of increased internal blastomere movement and lysis upon arrest (FIG. 5E), which was not observed in Msk2 mRNA rescued blastocysts). We note that this phenotype resembled the aberrant mitosis and cell death observed during mitotic catastrophe. Perhaps, the lysis of blastomeres with abnormal mitotic divisions induced by Msk2-mediated knockdown may constitute a mechanism for mouse embryos to avoid chromosomal instability and explain the low aneuploidy rates observed in mice. In support of this, we immunostained mouse embryos with LaminB1, a nuclear envelope marker, and observed the formation of LaminB1 encapsulated micronuclei in Msk2- injected (indicated by white arrows), but not 3'COF-injected embryos prior to lysis (FIG. 5F).

Association Between MSK2 Expression, Mitosis and Aneuploidy in Human Embryos.

Figure 6:
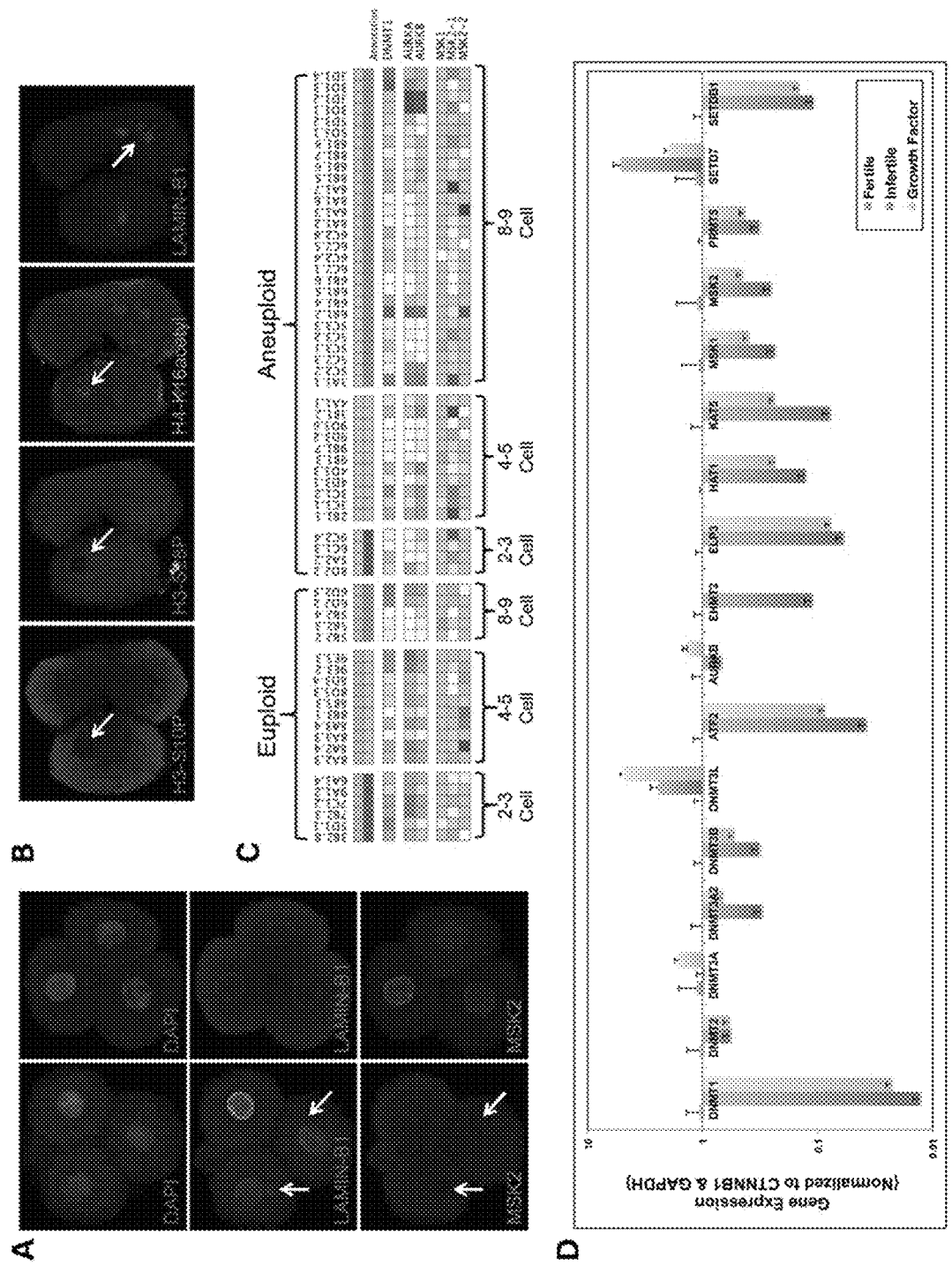
FIG. 6. Association between mitosis, aneuploidy and the expression of epigenetic regulators in human embryos. (A) Human zygotes were cultured until the 4-cell stage and previously identified cell cycle parameters predictive of blastocyst formation and ploidy status were measured by time-lapse image analysis. Embryos with abnormal parameter timing and micronuclei exhibited low MSK2 expression, whereas high MSK2 expression was observed in embryos with intact primary nuclei and normal parameter timing. (B) A lack of both H3-S10P and H3-S28P, two of the histone modifications that MSK2 mediates, was also observed in embryos with micronuclei in contrast to elevated H4-K16acetyl, which has been shown to be involved in DNA repair and apoptosis. (C) Gene expression analysis of embryos determined to be euploid or aneuploid by A-CGH. Note the high levels of expression in both MSK2 isoforms in euploid embryos particularly when comparing to housekeeping gene expression levels. (D) Comparison of DNMT and histone-modifying enzyme expression in fertile, infertile and GFC-treated blastocysts (N=6 to 8 embryos from each group) by Q-PCR demonstrates that growth factor supplementation can partially restore the expression of epigenetic regulators to levels observed in embryos from fertile patients.

Given our findings that the embryo arrest in Msk2 MO-injected embryos was associated with mitotic arrest and blastomeric lysis, our next aim was to determine whether MSK2 was involved in abnormal mitotic divisions and possible aneuploidy generation in human embryos. Our experimental design for this is as shown in FIG. 1B and made use of previous studies. By measuring previously identified cell cycle parameters predictive of blastocyst formation prior to embryonic genome activation (Wong et al. Nat Biotechnol 28, 1115-1121 (2010)) we recently demonstrated that blastomere behavior reflects human embryo ploidy by the 4-cell stage (Chavez et al. Nat Commun 3, 1251 (2012)) and that chromosome-containing micronuclei/fragments may contribute to the complex aneuploidy observed in cleavage-stage human embryos (Johnson et al. (2010) Hum Reprod 25, 1066-1075). Therefore, we similarly analyzed cell cycle parameter timing in human embryos cultured from the zygote to approximately the 4-cell stage using time-lapse imaging and evaluated each embryo for the expression of MSK2 and LAMIN-B1 (FIG. 1B). As FIG. 6A demonstrates, we detected low MSK2 expression in blastomeres with visible micronuclei (indicated by white arrows) and abnormal cell cycle parameters, whereas high MSK2 expression was observed in blastomeres with intact primary nuclei and normal parameter timing. In those embryos with micronuclei, we also observed a lack of both H3-S10 and H3-S28 phosphorylation, two of the histone modifications that MSK2 mediates, but not H4-K16 acetylation, which has been shown to be involved in DNA repair and programmed cell death (FIG. 6B). The absence of MSK2 expression is related to both abnormal mitotic divisions and micronuclei formation and can contribute to aneuploidy generation in human embryos.

Figure 13:
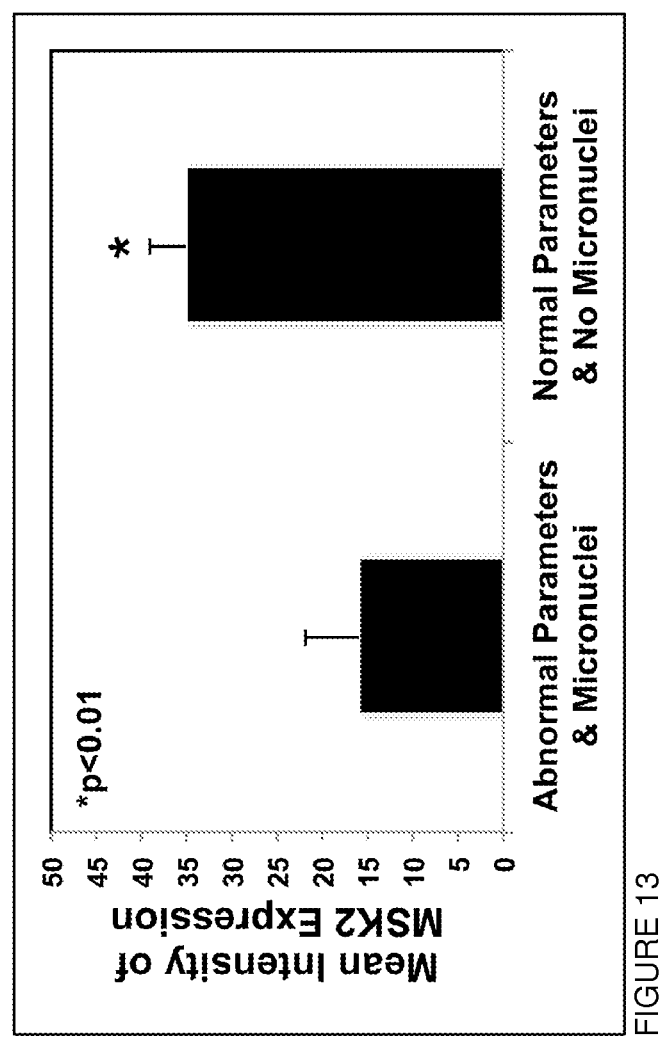
FIG. 13 Semi-quantitative measurement of MSK2 expression in human embryos. Human zygotes were cultured until the 4-cell stage and previously identified cell cycle parameters predictive of blastocyst formation (1) and ploidy status (2) were measured by time-lapse image analysis. Embryos with abnormal parameter timing and micronuclei (N=6) exhibited lower MSK2 expression in comparison to embryos with intact primary nuclei and normal parameter timing (N=6) when quantified by measuring the mean pixel intensity of MSK2 immunostaining in each blastomere.

To further investigate the role of MSK2 in human pre-implantation development, we analyzed the expression of both full-length MSK2 (MSK2-2) as well an alternative splice variant (MSK2-1; Table 3), which does not exist in the mouse, in single blastomeres from cleavage-stage embryos that were determined to be either euploid (FIG. 13A) or aneuploid (FIG. 13B) by Array-Comparative Genomic Hybridization (A-CGH). Due to the high rates of mosaicism in human embryos at the cleavage stage, only embryos with blastomeres that exhibited similar A-CGH profiles (N=12) were included in the analysis. While both MSK2 isoforms were more highly expressed in the blastomeres of euploid embryos, low to moderate levels MSK2 expression were detected in aneuploid embryos (FIG. 6C) to support a role for MSK2 in the regulation human embryonic aneuploidy generation. Given that between 50-80% of cleavage stage human embryos are chromosomally abnormal, this may also help explain why MSK2 expression was only detected in a few blastomeres from human embryos at the 8-cell stage (FIG. 2D). In addition, DNMT1 and AURKB were also expressed in a similar pattern as MSK2 expression in euploid and aneuploid embryos to suggest an association between MSK2, DNMT1 and AURKB function.

TABLE 3

| Gene Name | Forward Primer | Reverse Primer |
|---|---|---|
| DNMT1 | 5'-GCCATTGGCTTGG AGATCA (SEQ ID NO: 1) | 5'-AGCAGCTTCCTCCT CCTTTA-3' (SEQ ID NO: 2) |
| AURKA | 5'-GGTGGTCAGTACA TGCTCCA (SEQ ID NO: 3) | 5'-GCATCCGACCTTCA ATCATTTCA-3' (SEQ ID NO: 4) |
| AURKB | 5'-ATGGAGAATAGCA GTGGGACAC-3' (SEQ ID NO: 5) | 5'-CAGAGGACGCCCAA TCTCAA-3' (SEQ ID NO: 6) |
| MSK1 | 5'-CGGCTAAAGCCAC CGGATAA-3' (SEQ ID NO: 7) | 5'-TAAAGGCGTGGAAG GTTGCT-3' (SEQ ID NO: 8) |
| MSK2-1 | 5'-CGTGTATGGGGGT GAGATCG-3' (SEQ ID NO: 9) | 5'-GGGCGAGTCCTGCA TCATAG-3' (SEQ ID NO: 10) |
| MSK2-2 | 5'-CCTTCCCTGCAAC TCTATCTGG-3' (SEQ ID NO: 11) | 5'-GGACTGTCCTTTCC TCTCCTACC-3' (SEQ ID NO: 12) |

Sequence of primers used for gene expression analysis in single human blastomeres. The gene name and sequence of each forward and reverse primer used for Quantitative-PCR analysis in the study.
Note that the primers were designed to span exons in order to distinguish between cDNA and genomic DNA products.

Growth Factor Supplementation Restores Epigenetic Expression Levels in Human Embryos.

Based on previous studies suggesting that media supplementation of certain autocrine/paracrine factors can enhance oocyte maturation and early embryo development (Anderson et al. Fertil Steril 93, 1394-1406 (2010); Ye et al. Reprod Biomed Online 19, 181-190 (2009)), our final objective was to determine whether the addition of defined factors to culture media had any effects on the expression of epigenetic regulators in human embryos by microfluidic Q-PCR (FIG. 1B). For this purpose, we evaluated DNMT and histone-modifying enzyme expression in embryos cultured with a growth factor cocktail containing BDNF, IGF-I, EGF, GM-CSF, FGF2 and GDNF, which were selected based on the aforementioned studies, as well as the confirmation of their corresponding receptor expression in human oocytes (McElroy et al. (2010) PLoS One 5, e10979). By comparing gene expression in human zygotes cultured either in the absence (FIG. 2B) or the presence of the cocktail until the 2-cell to blastocyst stage, we determined that growth factor supplementation induced changes in DNMT and histone-modifying enzyme expression beginning at the 8-cell stage (FIG. 6C).

Figure 14:
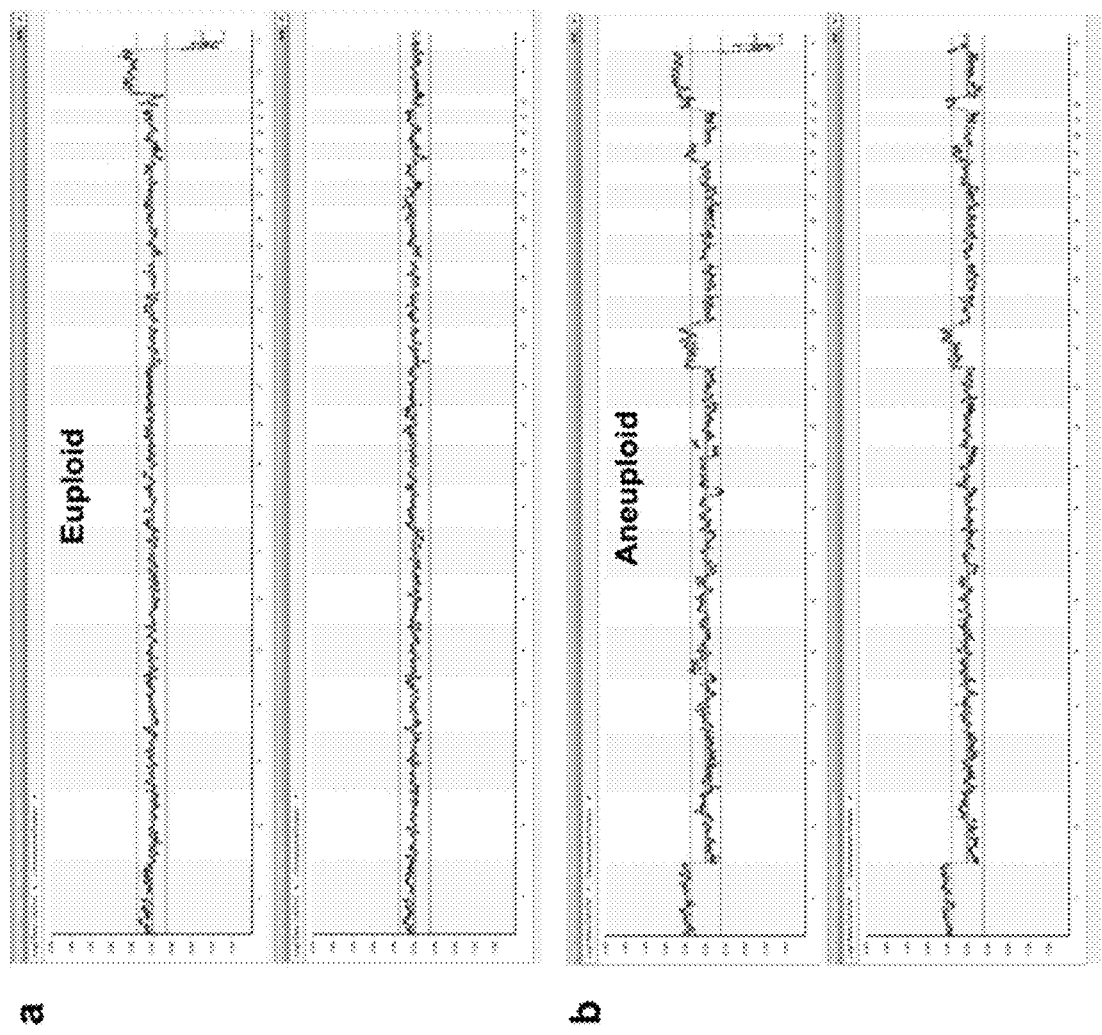
FIG. 14. Assessment of complete ploidy status in single human blastomeres. Human zygotes were cultured until the 8-cell stage and previously identified cell cycle parameters predictive of successful blastocyst formation (1) and ploidy status (2) were measured via time-lapse image analysis. Following parameter measurement, cleavage-stage human embryos were disassembled into single blastomeres and half of the cells were analyzed by Array-Comparative Genomic Hybridization (A-CGH) to determine whether (a) euploid or (b) aneuploid while the other half of the cells were evaluated by single blastomere Q-PCR (FIG. 6c) for comparison.
Figure 15:
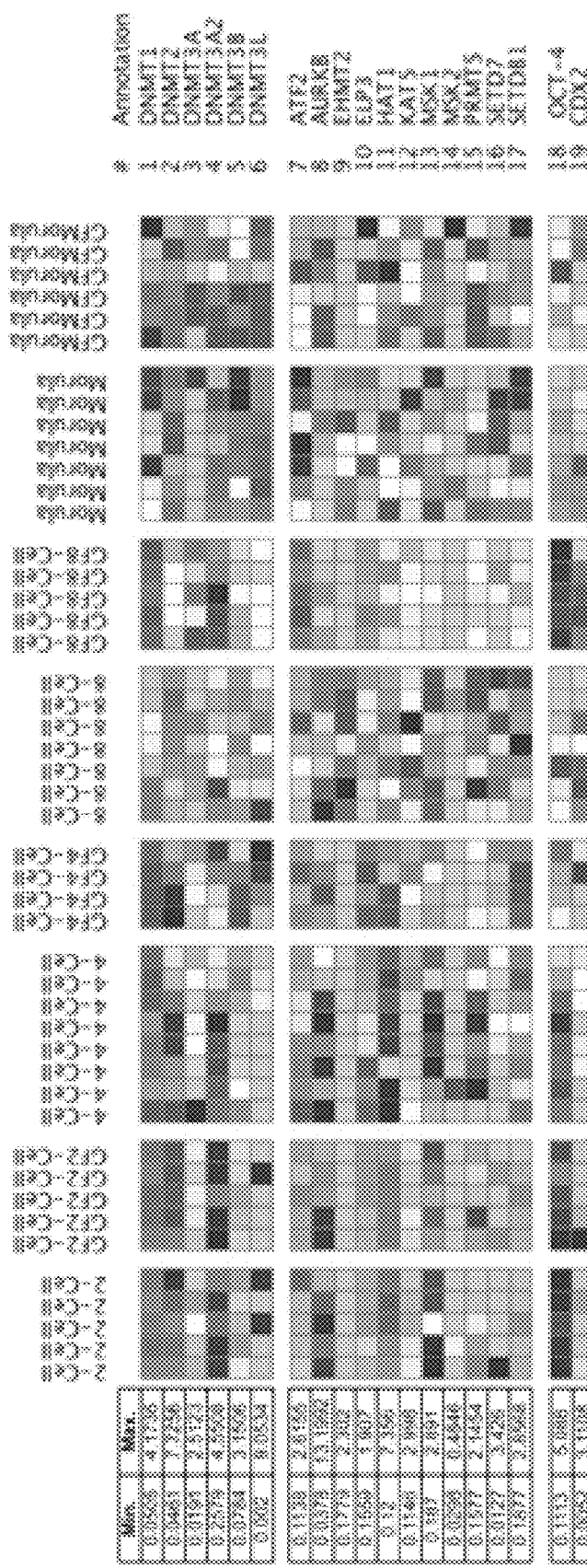
FIG. 15. Growth factor supplementation influences epigenetic expression levels. Human zygotes were cultured in the absence or presence of a growth factor cocktail (GFC) until the 2-cell to morula stage and the expression of DNA methyltransferases (DNMTs), histone-modifying enzymes, OCT-4 and CDX2 was evaluated by quantitative RT-PCR (Q-PCR). Note the change in epigenetic regulator and cell lineage expression upon GFC addition beginning at the 8-cell stage of development. Grey squares indicate no expression, whereas blue, white and red squares correspond to low, medium and high expression, respectively. The range of expression levels for each gene is as shown on the left with the minimum (Min.) and maximum (Max.) values.

Although similar blastocyst formation rates (~30%) were observed with human zygotes cultured in the absence or presence of the growth factor cocktail, comparison of gene expression between the two groups revealed that media supplementation induced changes in DNMT and histone-modifying enzyme expression beginning at the 8-cell stage (FIG. 14). Analysis of epigenetic regulator expression in blastocysts from both fertile and infertile patients also revealed differences in DNMT and histone-modifying enzyme expression levels (FIG. 6D). More importantly, when epigenetic regulator expression was compared in infertile, fertile and growth factor treated blastocysts, we determined that media supplementation either partially or fully restored the expression levels of several DNMTs and histone-modifying enzymes, including MSK2, to that observed in embryos from fertile patients (FIG. 6D). Thus, our data suggests that the addition of growth media may potentially reduce chromosomal instability and improve IVF outcomes by positively influencing the expression of epigenetic regulators in human embryos.

Figure 7:
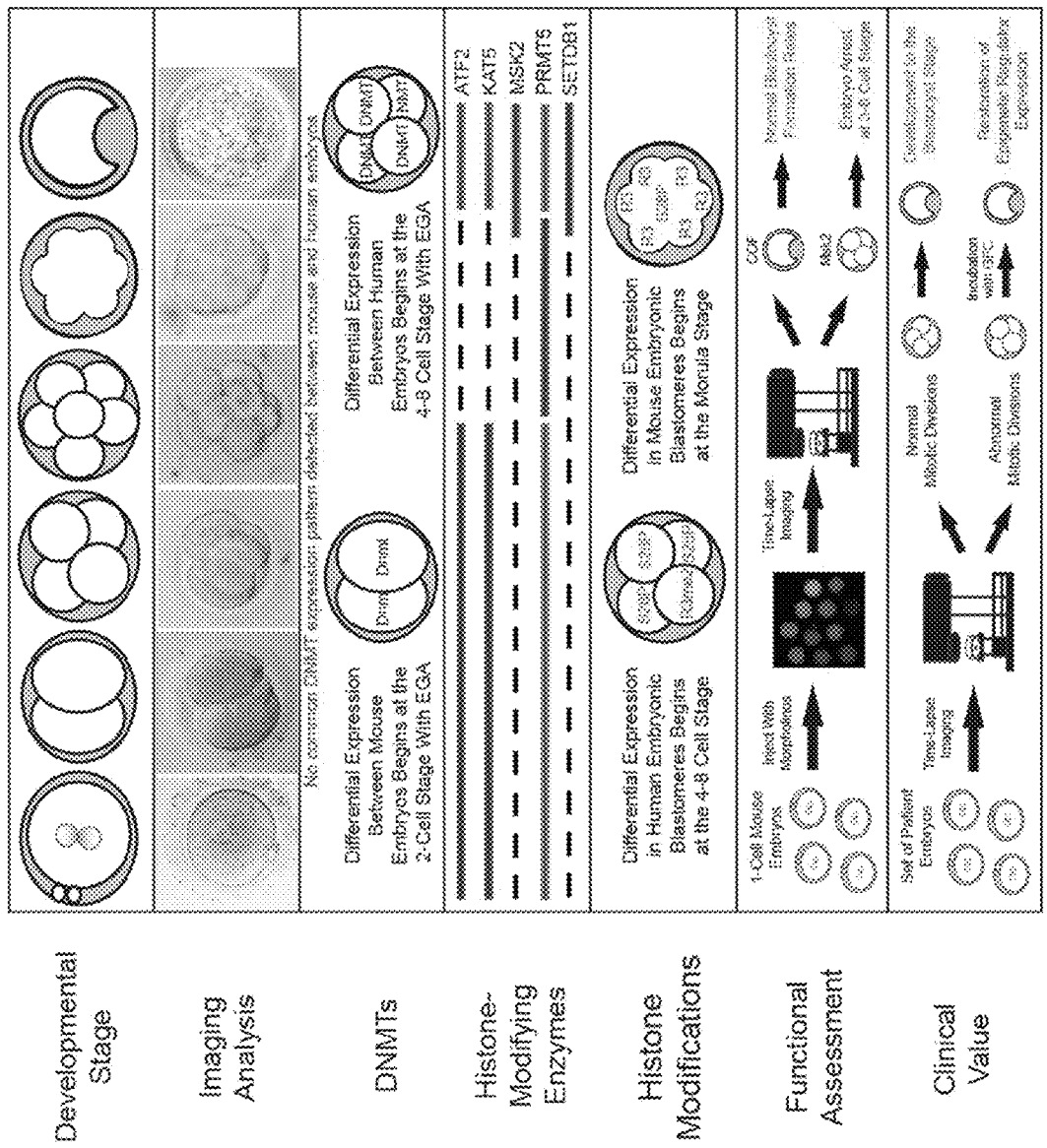

This study directly compares DNA methylation and histone modification expression patterns in both the mouse and human, individual embryos and single cells, at the mRNA as well as protein level, in embryos from fertile and infertile couples and following growth factor supplementation. We validate our findings by demonstrating a functional role for a particular epigenetic regulator in mouse and human pre-implantation development. While DNMT expression patterns differed substantially between mouse and human embryos, mRNA expression levels and timing of the histone-modifying enzymes, ATF2, KAT5, MSK2, PRMT5 and SETDB1 were similar in these two species. Since both ATF2 and KAT5 are involved in the acetylation of lysine residues, MSK2 in the phosphorylation of serine residues, PRMT5 in the methylation of arginine residues and SETDB1 in the methylation of lysine residues, this suggests that expression of at least one member from each histone-modifying enzyme class is conserved between human and mouse development (FIG. 7).

The greatest variation in DNMT, histone modification and histone-modifying enzyme expression was observed between human embryos beginning at the 4- to 8-cell stage, which we attributed, at least in part, to differences between single cells within the same embryo. We previously demonstrated by single cell gene expression profiling that human blastomeres develop cell autonomously, and this is supported by the findings presented here since we show that individual blastomeres within the human embryo can simultaneously express different epigenetic marks. Given that some of these epigenetic markers are differentially associated with mitosis, DNA repair and transcriptional activation and/or silencing, these findings also support a divergent developmental potential for blastomeres of the human embryo at the 4- to 8-cell stage (FIG. 7).

In order to functionally validate our findings, we reduced expression of the histone-modifying enzyme, Msk2, and examined the effects in the mouse for potential correlation to human pre-implantation development. While knockout mice for Msk2 are reported to be viable and fertile, other studies have shown that Msk1/Msk2 double knockout mice exhibit hypersentivity to endotoxic toxic and prolonged inflammation and that residual histone phosphorylation is still observed to suggest at least some functional redundancy. Following injection of the Msk2-MO in 1-cell embryos here, we observed almost complete embryo arrest at the 3-8-cell stage and an unusual phenotype in which increased cell movement and eventual blastomere lysis was detected. Based on the observations that reduced Msk2 expression had effects on the expression of Dnmt1 and Aurkb, both of which are known to have important roles in mitosis and possibly ploidy, this suggests that the embryo arrest observed after Msk2 injection is likely due to a defect in mitosis. In addition, we further suggest that the blastomere lysis observed following Msk2 MO injection resembles cellular events described during mitotic catastrophe, may represent a mechanism for embryos to avoid chromosomal instability and explain the low aneuploidy rates observed in mice. A correlation between MSK2 expression and human aneuploidy generation is supported by our findings of abnormal cell cycle parameter timing, ploidy status, micronuclei formation, reduced MSK2 expression, and alterations in histone modifications mediated by MSK2, in human embryos (FIG. 7), the latter of which has similar indications in lower organisms.

Finally, while we did observe differences in epigenetic expression profiles between fertile and infertile patient embryos, the incubation of embryos from infertile couples with a growth factor cocktail either partially or fully restored the expression levels of numerous epigenetic factors beginning at the 8-cell stage when the major wave of embryonic genome activation occurs. This suggests that the addition of certain growth factors to embryo culture media can prevent alterations in epigenetic profiles (FIG. 7) and improve developmental competence of patient embryos subjected to culture. These findings demonstrate that although epigenetic mechanisms do not alter DNA sequence, they have essential roles for pre-implantation development and possible pregnancy outcomes, especially in the context of IVF. The work described here contributes to our understanding of the epigenetic requirements for normal embryogenesis and in cases of human reproductive failure.

Materials and Methods

Sample source and procurement. Approximately 150 supernumerary human embryos subsequently donated for non-stem research were obtained with written informed consent from the Stanford University Regenerative Medicine through the Ethical procurement of Nonviable or Excess cellular Waste (RENEW) Biobank and the Reproductive Medicine Center at the University of Minnesota, which received embryos from the Lutheran General Hospital IVF Program (Park Ridge, Ill.) when it closed in 2002. De-identification and molecular analysis was performed according to the Stanford University Institutional Review Board (IRB)-approved protocol #10466 entitled "The RENEW Biobank" and the University of Minnesota IRB-approved protocol #0306M49242 entitled "Stage-Specific Genomic Characterization of Human Preimplantation Embryos." No protected health information was associated with each of the embryos. The average maternal age was 34 years old and the most common cause of infertility was unexplained at 35% of couples (Kalista, T. et al. Cell Stem Cell 8, 360-362 (2011)). Embryos from patients classified as fertile was based on the use of donor materials for IVF cycles and the inclusion of embryos from fertile couples seeking gender selection or Human Leukocyte Antigen (HLA) typing.

Human embryo thawing and culture. Human embryos were thawed by a 2-step rapid thawing protocol using Quinn's Advantage Thaw Kit (CooperSurgical, Trumbull, Conn.) as previously described (Shu, Y. et al. Fertil Steril 91, 401-406 (2009)). In brief, either cryostraws or vials were removed from the liquid nitrogen and exposed to air before incubating in a 37° C. water bath. Once thawed, embryos were transferred to a 0.5-mol/L sucrose solution for 10 minutes followed by a 0.2-mol/L sucrose solution for an additional 10 minutes. The embryos were then washed in Quinn's Advantage Medium with Hepes (CooperSurgical) plus 5% Serum Protein Substitute (SPS; CooperSurgical) and each transferred to a 20 ul microdrop of either Quinn's Advantage Cleavage Medium (CooperSurgical) supplemented with 10% SPS between Day 1 to 3 or Quinn's Advantage Blastocyst Medium (CooperSurgical) with 10% SPS after Day 3 under mineral oil (Sigma, St. Louis, Mo.). Approximately half of the embryos were also cultured in the presence of a growth factor cocktail containing 10 ng/ml BDNF (PeptroTech Inc., Rocky Hill, N.J.), 40 ng/ml IGF-I (Sigma-Aldrich, St. Louis, Mo.), 5 ng/ml EGF (R&D Systems, Inc., Minneapolis, Minn.), 2 ng/ml GM-CSF (R&D Systems, Inc.), 0.5 ng/ml FGF2 (R&D Systems, Inc.) and 10 ng/ml of GDNF (R&D Systems, Inc.). All embryos were cultured at 37° C. with 6% CO2, 5% O2 and 89% N2 and embryo development was monitored daily by microscope for up to 7 days.

Mouse embryo collection and culture. 3-5 week old wild type C57BL6×DBA/2 (B6D2F1) female F1 mice were obtained from Charles River (Hollister, Calif.) and superovulated by intraperitonial injections of 10 IU of Pregnant Mare's Serum Gonadotropin (PMSG; Sigma) followed by 5-10 IU of human Chorionic Gonadotropin (hCG; Sigma) 48 hours later and mated overnight with wild type B6D2F1 male mice. Females were sacrificed by cervical dislocation approximately 18 hours after hCG injection and their oviducts, along with the adjacent uterine and ovarian tissue, were removed and transferred to EmbryoMax M2 Medium (Millipore, Billerica, Mass.) for dissection. 1-cell embryos were released from the oviducts by gently tearing the oviduct with a 25 Gauge ⅝" needle syringe under a stereomicroscope. Cumulus cells were removed from the embryos by hyaluronidase (Sigma) treatment and gentle pipetting. Two pronuclei stage embryos were recovered, pooled from 8-10 females in M2 media and cultured in Quinn's Advantage Cleavage Medium (CooperSurgical) with 10% SPS at ten embryos per 20 μL microdrop under mineral oil at 37° C. with 6% CO2, 5% O2 and 89% N2. All procedures involving animals were performed under the Institutional Animal Care and Use Committee (IACUC) protocol #16146 entitled "Molecular Analysis of Embryogenesis and Gametogeneis," which was approved by the Administrative Panel on Laboratory Animal Care (APLAC) at Stanford University.

Time-lapse imaging and parameter analysis. Embryo development was monitored using a custom-built miniature microscope system consisting of 2 inverted digital microscopes, each with LED illumination, 10× Olympus objective, manual focus knob and a 5 megapixel CMOS camera. The microscopes were modified for darkfield illumination by placing a darkfield aperture between the collimated white LED and the condenser lens as previously described (Wong et al. Nat Biotechnol 28, 1115-1121 (2010)) and connected to an external PC via USB cables that passed through the rear access port of the incubator. Images were taken at a 0.6 second exposure time every 5 minutes for up to 5 days and a custom software program (written in C++) was used to control the microscopes, provide a user interface and save the images to file. After each experiment, images were compiled into a time-lapse movie with well identification labels and timestamps that allowed manual measurement of the imaging parameters.

Single embryo and cell gene expression analysis. Gene expression was analyzed in mouse and human embryos using the BioMark Dynamic Array microfluidic system (Fluidigm Corp., So. San Francisco, Calif.). The zona pellucida (ZP) was removed by treatment with Acidified Tyrode's Solution (Millipore) and ZP-free embryos were washed in Quinn's Advantage Medium with Hepes plus 5% SPS three times and then quick frozen in Phosphate Buffered Solution (PBS; Invitrogen, Carlsbad) with 0.1% Bovine Serum Albumin (BSA; Sigma-Aldrich) on dry ice for storage at −80° C. until use. Cleavage stage human embryos were dis-assembled to single cells in Quinns Advantage Medium with HEPES (Ca and Mg Free; Copper Surgical) plus 10% Human Albumin (Cooper Surgical), while mouse embryos at the cleavage stage were dissembled in 0.25% Trypsin-EDTA (Gibco) plus 10% Human Albumin both at 37° C. with gentle pipetting. Individual embryos and single cells were pre-amplified according to the manufacturer's protocol (Fluidigm Corp.) using the CellsDirect One-Step qRT-PCR kit (Invitrogen) and 20× TaqMan gene expression assays (Applied Biosystems, Foster City, Calif.). Together with 2.5 ul 2× Universal Master Mix (Applied Biosystems) and 0.25 ul Sample Loading Buffer (Fluidigm Corp.), 2.25 ul pre-amplified cDNA was loaded into the sample inlets of either a 48.48 or a 96.96 Dynamic Array (DA; Fluidigm Corp.). For each probe, 2.5 ul 20× TaqMan gene expression assay and 2.5 ul Assay Loading Buffer (Fluidigm Corp.) was loaded into the assay inlets on the DA. Each sample was assayed in triplicate and the expression of between 6 and 10 housekeeping genes were analyzed as a control. Any single mouse or human embryo or blastomere that did not contain robust expression of all housekeeping genes analyzed was removed. Calculated normalized relative quantity (CNRQ) values were calculated and normalized to the 2 or 3 most stable housekeeping genes using the qBasePlus 1.3 analysis software as previously described and graphed using Gene-E.

Antibodies.

The Histone H3-S10P mouse monoclonal antibody (clone 6G3) was purchased from Cell Signaling Technology, Inc. (Danvers, Mass.), whereas the H3-S28P rat monoclonal (clone HTA28) and the H4-R3me2 rabbit polyclonal antibody (catalog #39275) were obtained from Thermo Fisher Scientific (Rockford, Ill.) and Active Motif (Carlsbad, Calif.), respectively. The Histone H3-K4me3 rabbit monoclonal antibody (clone MC315) was purchased from Millipore, while the Histone H4-K16acetyl goat polyclonal antibody (catalog #sc-8662) was obtained from Santa Cruz Biotechnology, Inc (Santa Cruz, Calif.). The Msk2 rabbit polyclonal (catalog # ab42282), Lamin-B1 rabbit polyclonal (catalog #ab16048) and Gapdh rabbit polyclonal (catalog #ab9485) antibodies were obtained from Abcam (Cambridge, Mass.).

The Alexa Fluor donkey anti-mouse 405 antibody (custom synthesis), donkey anti-rat 488, donkey anti-sheep 488, donkey anti-goat 568 and donkey anti-rabbit 647 antibodies were purchased from Invitrogen (Carlsbad, Calif.) for confocal imaging analysis. As controls, the mouse, rat, rabbit and goat IgG isotype antibodies were obtained from Vector Laboratories (Burlingame, Calif.).

Confocal imaging analysis and 3-dimensional modeling. ZP-free mouse and human embryos were obtained as described above and washed in PBS plus 0.1% BSA and 0.1% Tween-20 (PBS-T; Sigma-Alrdrich) before fixation in either 100% cold methanol for 20 minutes at −20° C. or 4% paraformaldehyde in PBS (USB Corp., Cleveland, Ohio) for 20 min. at Room Temperature (RT). Once fixed, the embryos were washed three times in PBS-T to remove any residual fixative and permeabilized in 1% Triton X-100 (Sigma-Aldrich) for 1-2 hours at RT. Following permeabilization, the embryos were washed three times in PBS-T and then blocked in 4% normal donkey serum (Jackson ImmunoReasearch Laboratories, Inc., West Grove, Pa.) in PBS-T overnight at 4° C. The embryos were incubated w/ primary antibodies in PBS-T with 1% donkey serum sequentially for 1 hour each at RT at the following dilutions: mouse H3-S10P (1:200), rat H3-S28P (1:200), rabbit H4-R3me2 (1:1,000), rabbit H3-K4me3 (1:200) and goat H4-K16Ac (1:200) over the span of 1-2 days and/or with rabbit Msk2 (1:400) and Lamin-B1 (1:1,000). Primary signals were detected using the appropriate 405, 488, 568 or 647-conjugated donkey Alexa Fluor secondary antibody (Invitrogen) at a 1:250 dilution at RT for 1 hour in the dark. The embryos were washed three times with PBS-T between each primary and secondary antibody incubation as well as prior to the next primary antibody incubation. Immunofluorescence was visualized by sequential imaging, whereby the channel track was switched each frame to avoid cross-contamination between channels, using a Zeiss LSM510 Meta inverted laser scanning confocal microscope. The instrument settings, including the laser power, pinhole and gain, were kept constant for each channel to facilitate semi-quantitiative comparisons between developmental stages and mouse and human embryos. Confocal sections were captured at 1 mm intervals throughout the whole embryo and processed in ImageJ (NIH) for Z-stack imaging analysis. Three-dimensional reconstructions of embryos were accomplished with IMARIS (Bitplane).

Mouse embryonic germ (mEG) cell culture. Undifferentiated mEGs, which were isolated from a E8.5 mouse embryo as previously described (Onyango, P. et al. Proc Natl Acad Sci USA 99, 10599-10604 (2002)), were cultured on irradiated STO feeders (ATCC, Manassas, Va.) in EG medium consisting of High Glucose DMEM (Gibco) supplemented with 15% FBS (Hyclone), 200 mM GlutaMAX-1 (Gibco), 10 mM minimal essential medium (MEM) nonessential amino acids (Gibco), 100 U/ml penicillin/streptomycin (Gibco), 0.1 mM b-mercaptoethanol (Chemicon; Billerica, Mass.) and 106 units/l ESGRO (LIF; Chemicon) according to (Fox, M. S. et al. Dev Biol 301, 417-431 (2007)) and maintained at 37° C./5% CO2. The 8.5 mEGs were grown to 70% confluence and passaged using 0.05% Trypsin-EDTA (Gibco) to Matrigel Basement Membrane Matrix (BD Biosciences, Sparks, Md.) containing Falcon 6-well plates (BD Biosciences) to remove the contaminating STO feeders prior to nucleofection.

Nucleofection of antisense morpholino oligonucleotides. The expression of Msk2 was knocked down in 8.5 mEGs using a Morpholino oligonucleotide (MO), which targets the 5' UTR through the first 25 bases of the coding sequence of the enzyme, from Gene Tools, LLC (Philomath, Oreg.). In contrast to other gene knockdown strategies, MOs function via an RNase H- and Dicer-independent steric hindrance mechanism and are therefore, free of the widespread off-target effects typical of knockdowns that rely on RISC or RNase-H activity. Rather than degrading their RNA targets, MOs block mRNA translation in the cytosol by inhibiting the translation initiation complex (Curr Top Med Chem 7, 651-660 (2007)). Undifferentiated 8.5 mEGs were nucleofected with 100 M of each MO or mock transfected with water using the Cell Line 96-well Nucleofector SF Kit and the 96-well Nucleofector shuttle according to the manufacturer's protocol (Lonza, Basel, Switzerland). In brief, approximately 5×105 8.5 mEGs were nucleofected per well using the CM-113 shuttle program, which was previously determined to result in high transfection efficiency with minimal effects on mEG cell viability using the Cell Line Optimization 96-well Nucleofector Kit (Lonza). An unlabeled Random Control and/or 3'-carboxyfluorescein labeled standard control MO purchased from Gene Tools, LLC were used as negative controls.

Western Blot analysis. Following nucleofection, 8.5 mEGs were lysed in Ripa buffer (Sigma-Aldrich) in the presence of a protease inhibitor cocktail (Roche Applied Science, Indianapolis, Ind.). Protein concentrations were calculated by BCA assay (Pierce Biotechnology, Rockford, Ill.). 20 µg of total cellular protein was loaded per lane and separated under reducing conditions by SDS-PAGE using 10% polyacrylamide gels and transferred to PVDF membranes (GE Healthcare, Piscataway, N.J.). The membranes were stained with Ponceau Red (Sigma-Aldrich) to ensure efficient transfer and equal loading of proteins. To inhibit nonspecific binding, membranes were blocked with 5% powdered milk in PBS/0.1% Tween-20 (PBS-T) prior to immunblotting. The membranes were then incubated with primary antibody (1:500 Msk2; 1:10,000 Gapdh) overnight at 40 C followed by a 1:10,000 dilution of donkey anti-rabbit Horse Radish Perioxidase (HRP)-conjugated secondary antibody (GE Healthcare) for 1 hour at room temperature in PBS-T/1% powdered milk. Following each step, the membranes were washed three times with PBS-T for 10 minutes. Finally, the blots were developed using the enhanced chemiluminescence (ECL) system (GE Healthcare) and an All-Pro Imaging film developer (Melville, N.Y.). As a negative control, membranes were incubated with secondary antibody alone to validate the specificity of the signal.

Microinjection of antisense morpholino oligonucleotides. Initial concentrations of 0.05 to 0.6 mM of 3'-carboxyfluorescein-labeled morpholino were injected into mouse zygotes based on previous findings (Foygel, K. et al. PLoS One 3, e4109 (2008)) and it was determined that 0.3 mM of the standard control was the maximum concentration that would allow normal rates of blastocyst development. Therefore, a similar concentration of Msk2 morpholino with the sequence 5'-CCTCGTCCTCATCCTCGTCTCCCAT-3' (SEQ ID NO:13), which was designed to target the translation start site of Msk2 and labeled with 3'-carboxyfluorescein for visualization, was injected into the cytoplasm of each embryo using a CellTram vario (Eppendorf, Hauppauge, N.Y.), electronic microinjector (Naraishige 1M300, Japan) and Transferman NK 2 Micromanipulator (Eppendorf). Non-injected, water injected and the injection of a 3' carboxyfluorescein labeled standard control MO that does not target any known sequence in the mouse genome or transcriptome served as controls in each experiment to assess enzyme-MO-mediated knockdown. Each MO was prepared in water and incubated at 6500 for 10 minutes prior to injection.

Generation of modified Msk2 mRNA for rescue. The Msk2 open reading frame (ORF) was amplified by PCR from a mouse Msk2 plasmid (Origene Rockville, Md.) using the HiFi Hotstart kit (KAPA Biosystems, Woburn, Mass.) and the following Msk2 mutagenic primers synthesized by the Stanford University Protein and Nucleic Acid (PAN) Facility: 5'-AAAAAGCTAGCCACCATGGGTGAC-GAAGACGAG-3 (SEQ ID NO:14)' and 5'-AAAAACCG-GTCTAGGAAGGGGACAAGG-3' (SEQ ID NO:15). In order to avoid direct targeting of the Msk2 morpholino to the rescue mRNA, the 5' region of the Msk2 mRNA was modified using the redundancy of the genetic code to ensure the rescue mRNA still coded for the same Msk2 protein. A "backbone sequence" containing 5' and 3' UTR regions, T7 promoter and a multiple cloning site was synthesized by DNA2.0 (Menlo Park, Calif.). Both the ORF and DNA2.0 vector containing the "backbone sequence" were digested with AgeI and NheI (New England Biolabs, Ipswich, Mass.) for 1 hour at 37° C., followed by gel purification (Qiagen, Valencia, Calif.). The digested ORF and DNA2.0 vector were ligated at RT for 2 hours using T4 ligase (New England Biolabs) and gel purified. Ligated products were transformed using chemically competent E. coli (Invitrogen) according to the manufacturer's instructions and insertion was verified by test digestion with Xbal (New England Biolabs). Clones with positive inserts were excised by similar restriction digest and purification (Qiagen) and a polyA tail was added by PCR using a T120-heeled reverse primer and purified (Qiagen) for in vitro transcription (IVT). Synthesis of modified mRNA was carried out with the MEGAscript T7 kit (Ambion, Grand Island, N.Y.) according to the manufacturer's instructions with a few modifications. A ribonucleoside mixture of 6 mM 3'-0-Me-m7G(5')ppp (5')G ARCA cap analog (New England Biolabs), 7.5 mM of adenosine triphosphate and 1.5 mM of guanosine triphosphate (Ambion), 7.5 mM of 5-methylcytidine triphosphate and pseudouridine triphosphate (TriLink Biotechnologies, San Diego, Calif.) was prepared and IVT reactions were incubated for 4 hours at 37° C., followed by DNase treatment for 15 min at 37° C. DNase treated RNA was purified using the MEGAclear kit (Ambion) and a 5'Cap was added by Antarctic Phosphatase (New England Biolabs) for 30 min at 37° C. and similarly purified. The Msk2 mRNA was analyzed by 1.5% denaturing formaldehyde-agarose gel and sequencing to verify the correct size of the transcript and specificity of the IVT reaction, respectively.

Statistical analysis. The data is represented as the average+the standard deviation and analyzed for statistical significance ($p<0.05$) using one-way ANOVA with the Bonferonni correction. All experiments were repeated three times with similar results.

What is claimed is:

1. A method for predicting blastocyst quality of a human embryo in vitro, the method comprising:
    analyzing expression of one or more genes associated with epigenetic regulation of gene expression wherein the genes associated with epigenetic regulation of gene expression are selected from ATF2, KAT5, MSK2, PRMT5, SETDB1, DNMT1 and AURKB;
    comparing the expression to a control sample;
    wherein altered expression levels are indicative of an greater potential for aneuploidy in the embryo, wherein an embryo or population of embryos assessed as having a low quality are cultured in medium supplemented with one or more of BDNF, IGF-I, estradiol, GDNF, leptin, FGF2, EGF, and GM-CSF.

2. The method of claim 1, wherein the gene is MSK2.

3. The method of claim 1, wherein the analysis is performed on a single cell of an embryo prior to the blastocyst stage.

4. A method for predicting blastocyst quality of a human embryo in vitro, the method comprising:
    analyzing expression of one or more genes associated with epigenetic regulation of gene expression wherein the genes associated with epigenetic regulation of gene expression are selected from ATF2, KAT5, MSK2, PRMT5, SETDB1, DNMT1 and AURKB;
    comparing the expression to a control sample; wherein altered expression levels are indicative of an greater potential for aneuploidy in the embryo, and
    selecting and implanting an embryo based on the assessment of quality.

5. The method of claim 1, where the embryonic cells are human pre-implantation embryos derived from oocytes that have been matured in vitro.

6. The method of claim 1, where the measurements are used to rank a group of embryos based on blastocyst quality.

* * * * *

SEQUENCE LISTING

```
<160> NUMBER OF SEQ ID NOS: 15

<210> SEQ ID NO 1
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 1
gccattggct tggagatca                                                  19

<210> SEQ ID NO 2
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 2
agcagcttcc tcctccttta                                                 20

<210> SEQ ID NO 3
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 3
ggtggtcagt acatgctcca                                                 20

<210> SEQ ID NO 4
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 4
gcatccgacc ttcaatcatt tca                                             23

<210> SEQ ID NO 5
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 5
atggagaata gcagtgggac ac                                              22

<210> SEQ ID NO 6
<211> LENGTH: 20
<212> TYPE: DNA
<213> ORGANISM: Artificial Sequence
```

```
<220> FEATURE:
<223> OTHER INFORMATION: synthetic polynucleotide

<400> SEQUENCE: 6
cagaggacgc ccaatctcaa                                                      20

<210> SEQ ID NO 7
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 7
cggctaaagc caccggataa                                                      20

<210> SEQ ID NO 8
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 8
taaaggcgtg gaaggttgct                                                      20

<210> SEQ ID NO 9
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 9
cgtgtatggg ggtgagatcg                                                      20

<210> SEQ ID NO 10
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 10
gggcgagtcc tgcatcatag                                                      20

<210> SEQ ID NO 11
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 11
ccttccctgc aactctatct gg                                                   22

<210> SEQ ID NO 12
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 12
ggactgtcct ttcctctcct acc                                                  23
```

```
<210> SEQ ID NO 13
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 13
cctcgtcctc atcctcgtct cccat                                           25

<210> SEQ ID NO 14
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 14
aaaaagctag ccaccatggg tgacgaagac gag                                  33

<210> SEQ ID NO 15
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 15
aaaaaccggt ctaggaaggg gacaagg                                         27
```